United States Patent [19]
Alcock et al.

[11] Patent Number: 5,736,188
[45] Date of Patent: Apr. 7, 1998

[54] PRINTED FLUID TRANSPORT DEVICES

[76] Inventors: Susan Alcock, The Granary, Uphoe Manor Farm, Harrold Road, Lavendon, Olney, Bucks MK46 4HX; Stephen White, 23 Normandy Close, Kempston, Bedford MK42 8TR; Anthony Turner, 8 Brook End, North Crawley, Bedfordshire; Steven Setford, 50 Barnards Hill, Marlow, Bucks SL7 2NZ; Ibtisam Tothill, 4 Thrift View, Bedford Road, Cranfield, Beds MK43 OHA; Jon Dicks, 8 Mountfield Close, Newport Pagnell, Bucks MK16 OJE; Sarah Stephens, 67 Bolingbroke Road, Stoke, Coventry CV3 1AP; Jennifer Hall, 4 Partridge Piece, Cranfield, Beds MK43 OBP; Phillip Warner, 15 Victoria Street, Wolverton, Milton Keynes MK12 5HG, all of United Kingdom

[21] Appl. No.: 512,358

[22] Filed: Aug. 8, 1995

[51] Int. Cl.⁶ .................... A01N 1/02; B05D 1/32; B05D 5/00
[52] U.S. Cl. .................. 427/2.11; 106/19 R; 427/2.13; 427/282; 435/4
[58] Field of Search ............... 427/282, 280, 427/286, 2.11, 2.13; 106/19 R; 435/4; 101/129

[56] References Cited

U.S. PATENT DOCUMENTS

| | | | |
|---|---|---|---|
| 3,418,158 | 12/1968 | Perry et al. | 210/314 |
| 3,667,607 | 6/1972 | Brandt | 210/198 |
| 4,503,144 | 3/1985 | Deeg et al. | 435/11 |
| 4,545,382 | 10/1985 | Higgins et al. | 128/635 |
| 4,604,264 | 8/1986 | Rothe et al. | 422/56 |
| 4,681,711 | 8/1989 | Friesen et al. | 436/7 |

(List continued on next page.)

FOREIGN PATENT DOCUMENTS

| | | |
|---|---|---|
| 0 127 958 A2 | 12/1984 | European Pat. Off. . |
| 0186286 A1 | of 1985 | European Pat. Off. . |
| 0186799 A1 | 12/1985 | European Pat. Off. . |
| 0191640 B1 | 2/1986 | European Pat. Off. . |
| 0202656 B1 | 5/1986 | European Pat. Off. . |
| 0239174 A1 | 3/1987 | European Pat. Off. . |

(List continued on next page.)

OTHER PUBLICATIONS

Newman J.D. et al., "Ink-jet Printing for the Fabrication of Amperometric Glucose Biosensors", *Analytica Chimica Acta*, 262:13–17, 1992.

Wang J. et al., "Screen-Printed Glucose Strip Based on Palladium-Dispersed Carbon Ink", *Analyst*, 119:1849–1851, Aug. 1994.

Athey et al., Avidin-Biotin Based Electromechanical Immunoassay for Thyrotropin, Ann. Clin. Biochem., 30:570–577 (1993).

(List continued on next page.)

*Primary Examiner*—Michael Lusignan

[57] ABSTRACT

A backing sheet (101) is provided with a pattern of pathways (131,132,133) of (e.g.) silica or cellulose by a printing process (e.g., screen printing). There may be multiple pathways leading from an eluant application region (117) to a detection zone (116) and thence to a waste reservoir (118). Different pathways may have different fluid traversal times because they differ in length and/or material (e.g., nitrocellulose for slow traversal and fibrous cellulose for rapid traversal by an aqueous liquid). Thus analyte and reagents deposited at depots (112,113) on different pathways are sequentially delivered to the detection zone. Reagents may be applied by printing. The detection zone may have an electrode assembly (105), also applied by printing, for detecting the effects of analyte.

8 Claims, 7 Drawing Sheets

U.S. PATENT DOCUMENTS

| | | | |
|---|---|---|---|
| 4,703,017 | 10/1987 | Campbell et al. | 436/501 |
| 4,711,245 | 12/1987 | Higgins et al. | 128/635 |
| 4,758,323 | 7/1988 | Davis et al. | 204/403 |
| 4,777,132 | 10/1988 | Green et al. | 435/25 |
| 4,790,640 | 12/1988 | Nason | 350/534 |
| 4,818,677 | 4/1989 | Hay-Kaufman et al. | 435/4 |
| 4,820,489 | 4/1989 | Rothe et al. | 422/56 |
| 4,820,636 | 4/1989 | Hill et al. | 435/14 |
| 4,830,959 | 5/1989 | McNeil et al. | 435/7 |
| 4,840,893 | 6/1989 | Hill et al. | 435/6 |
| 4,876,205 | 10/1989 | Green et al. | 436/66 |
| 4,888,816 | 12/1989 | Davis et al. | 436/518 |
| 4,900,424 | 2/1990 | Birth et al. | 204/409 |
| 4,912,041 | 3/1990 | Batchelor et al. | 435/101 |
| 4,931,385 | 6/1990 | Block et al. | 435/7 |
| 4,948,727 | 8/1990 | Cass et al. | 435/18 |
| 4,956,302 | 9/1990 | Gordon et al. | 436/161 |
| 4,966,671 | 10/1990 | Nylander et al. | 204/153.14 |
| 4,978,503 | 12/1990 | Shanks et al. | 422/58 |
| 4,980,298 | 12/1990 | Blake et al. | 436/518 |
| 5,124,253 | 6/1992 | Foulds et al. | 435/21 |
| 5,126,034 | 6/1992 | Carter et al. | 204/403 |
| 5,141,868 | 8/1992 | Shanks et al. | 435/288 |
| 5,185,247 | 2/1993 | Ismael | 435/14 |
| 5,194,133 | 3/1993 | Clark et al. | 204/299 R |
| 5,198,193 | 3/1993 | Bunce et al. | 422/100 |
| 5,202,261 | 4/1993 | Musho et al. | 435/288 |
| 5,223,438 | 6/1993 | Doi | 436/175 |
| 5,250,439 | 10/1993 | Musho et al. | 435/25 |
| 5,264,106 | 11/1993 | McAleer et al. | 204/403 |
| 5,281,539 | 1/1994 | Schramm | 436/518 |
| 5,282,950 | 2/1994 | Dietze et al. | 204/406 |
| 5,286,362 | 2/1994 | Hoenes et al. | 204/403 |
| 5,288,636 | 2/1994 | Pollman et al. | 435/288 |
| 5,326,449 | 7/1994 | Cunningham et al. | 204/403 |
| 5,360,595 | 11/1994 | Bell et al. | 422/56 |
| 5,378,332 | 1/1995 | Pandey | 204/153.12 |
| 5,383,346 | 1/1995 | Uenoyama et al. | 204/403 |
| 5,384,028 | 1/1995 | Ito et al. | 204/403 |
| 5,385,846 | 1/1995 | Kuhn et al. | 436/70 |
| 5,391,272 | 2/1995 | O'Daly et al. | 204/153.12 |
| 5,393,615 | 2/1995 | Corey et al. | 429/43 |
| 5,403,700 | 4/1995 | Heller et al. | 430/311 |
| 5,409,583 | 4/1995 | Yoshioka et al. | 204/153.12 |
| 5,411,647 | 5/1995 | Johnson et al. | 204/153.1 |
| 5,413,690 | 5/1995 | Kost et al. | 204/403 |
| 5,474,796 | 12/1995 | Brennan | 427/282 X |

FOREIGN PATENT DOCUMENTS

| | | |
|---|---|---|
| 0255291 B1 | 7/1987 | European Pat. Off. . |
| 02555291 A1 | 7/1987 | European Pat. Off. . |
| 0262328 A3 | 7/1987 | European Pat. Off. . |
| 0470649 A2 | 7/1987 | European Pat. Off. . |
| 0470649 A3 | 7/1987 | European Pat. Off. . |
| 0254202 B1 | 8/1987 | European Pat. Off. . |
| 0267724 B1 | 11/1987 | European Pat. Off. . |
| 0284232 A1 | 3/1988 | European Pat. Off. . |
| 0 262 328 A2 | 4/1988 | European Pat. Off. . |
| 0352138 A2 | 7/1989 | European Pat. Off. . |
| 0186799 B1 | 2/1990 | European Pat. Off. . |
| 0443231 A1 | 2/1990 | European Pat. Off. . |
| 0 262 328 A3 | 6/1990 | European Pat. Off. . |
| 0186286 B1 | 1/1991 | European Pat. Off. . |
| 0 127 958 B1 | 3/1992 | European Pat. Off. . |
| 0 262 328 B1 | 1/1993 | European Pat. Off. . |
| 0306772 B1 | 3/1993 | European Pat. Off. . |
| 0186799 B2 | 10/1993 | European Pat. Off. . |
| 2231150 B | 3/1990 | United Kingdom . |
| 012314 A3 | 8/1986 | WIPO . |
| WO 88/07666 | 10/1988 | WIPO . |
| WO 89/03992 | 5/1989 | WIPO . |
| WO 90/11519 | 10/1990 | WIPO . |
| WO 91/02589 | 3/1991 | WIPO . |
| WO 93/1045 | 5/1993 | WIPO . |
| WO 93/10457 | 5/1993 | WIPO . |
| WO 93/15404 | 8/1993 | WIPO . |
| WO 94/19683 | 9/1994 | WIPO . |
| WO 94/19684 | 9/1994 | WIPO . |

OTHER PUBLICATIONS

Bailey et al., Homogeneous Amperometric Immunoassay for Theophylline in Whole Blood Biosensor & Bioelectronics 8:415–419 (1993).

Bunce et al., Disposable Analytical Devices Permitting Automatic, Timed, Sequential Delivery of Multiple Reagents, Analytica Chemica Acta, 249:263–269 (1991).

Cardosi et al., An Electrochemical Immunoassay for *Clostridium perfringens* Phospholipase C, Electroanalysis 3:269–176 (1991).

Cardosi et al., An Electrochemical Immunoassay for Prostatic Acid Phosphatase Incorporating Enzyme Amplification; Immunoassay May 1989, pp. 50–58.

Cardosi et al., An Enzyme–Amplified Electrochemical Immunoassay for Thyrotropin; Electroanalysis, 1:297–304 (1989).

de Frutos et al., Tandem Chromatographic–Immunological Analyses Analytical Chemistry, 65(1):17–25 (1993).

Dong et al., Cholesterol Sensor based on Eletrodeposition of Catalytic Palladium Particles, Analytica Chemica Acta, 279:235–240 (1993).

Frew et al., Measurement of Alkaline Phosphatase Activity by Electrochemical Detection of Phosphate Esters, J. Electroanal. Chem., 266:309–316 (1989).

Gilmartin et al., Comparative Study of the Voltametric Behavior of Guanine at Carbon Paste and Glassy Carbon Electrodes and Its Determination in Purine Mixtures by Differential–pulse Voltametry, Analyst, 1613–1618 (1992).

Gilmartin et al., Development of Amperometric Sensors for Uric Acid Based on Chemically Modified Graphite–Epoxy Resin and Screen–printed Electrodes Containing Cobalt Phthalocyanine, Analyst, 119:243–252 (1994).

Gilmartin et al., Voltametric and Amperometric Behavior of Uric Acid at Bare and Surface–modified Screen–printed Electrodes: Studies Towards a Disposable Acid Sensor, Analyst, 117:1299–1303 (1992).

Gilmartin et al., Fabrication and Characterization of a Screen–printed, Disposable, Amerometric Cholesterol Biosensor; Analyst, 119:2331–2336 (1994).

Gilmartin et al., Novel, Reagentless, Amperometric Biosensor for Uric Acid Based on a Chemically Modified Screen–printed Carbon Electrode Coated With Cellulose Acetate and Uricase, Analyst, 119:833–840 (1994).

Hadas et al., A Rapid and Sensitive Heterogeneous Immunoelectromechanical Assay Using Disposable Electrodes, Journal of Immunoassay, 13(2):231–252 (1992).

Huet et al., Automatic Apparatus for Heterogeneous Enzyme Immunoassays Based on Electrocatalytic Detection of the Enzyme and Electrochemical Regeneration of the Solid Phase, Analytica Chimica Acta, 272:205–212 (1993).

Jackson et al., Determination of Serum Alkaline Phosphatase Activity by Electromechanical Detection with Flow Injection Analysis, J. Anal. Chem. 346;859–862 (1993).

Jenkins et al., The Use of Ion Pairing Reagents to Reduce Non-specific Adsorption in a Solid Phase Electromechanical Enzyme Immunoassay Journal of Clinical Immunoassay, 13(2):99–104 (Summer 1990).

Kronkvist et al., Determination of Drugs in Biosamples at Picomolar Concentrations Using Competitive ELISA with Electrochemical Detection: Application to Steroids, Journal of Phamaceutical & Biomedical Analysis, 11(6):459–467, (1993).

Kaku et al., Amperometric Enzyme Immunoassay for Urinary Human Serum Albumin Using Plasma–Treated Membrane, Analytica Chimica Acta, 272:213–220 (1993).

Koochaki et al., Electrode Responses to Phenolic Species Through Cellulosic Membranes, Journal of Membrane Sciences, 57:83–94 (1991).

La Salle et al., Utilization of a Nafion®–Modified Electrode in a Competitive Homogeneous Electromechanical Immunoassay Involving a Redox Cationic Labelled Hapten–Phenytoin, J. Electroanal. Chem., 350:329–335 (1993).

Limoges et al., Homogeneous Electrochemical Immunoassay Using a Perfluorosulfonated ionomer–Modified Electrode as Detector for a Cationic–Labeled Hapten, Anal. Chem., pp. 1054–1060 (1993).

Niwa et al., Small–Volume Voltametric Detection of 4–Aminophenol with Interdigitated Array Electrodes and its Application to Electrochemical Enzyme Immunoassay, Anal. Chem., 65:1559–1563 (1993).

Noble, Home Test for Cholesterol, Look, Ma, No Instrument, Analytical Chemistry, 65(23):1037A–1041A (1993).

O'Daly et al., Electrochemical Enzyme Immunoassay for Detection of Toxic Substances, Enzyme Micro. Technol., 14:299–302 (1992).

Palmer et al., Flow Injection Electromechanical Enzyme immunoassay for Theophylline Using a Protein A Immunoreactor and p–Aminophenyl Phosphate–p–Aminophenol as the Detection System, Analyst, 17:1679–1682 (1991).

Rishpon et al., Immunoelectrodes for the Detection of Bacteria, American Chemical Society, Chapter 6:59–71 (1992).

Schramm et al., Single–Step Electrochemical Immunoassay, pp. 252–259, no date.

Sittampalam et al., Surface–Modified Electromechanical Detector for Liquid Chromatography, Analytical Chemistry, 55:1608–1610 (1983).

Suzawa et al., New Approach for Sensitization of Solid––Phase Immunoassay Based on Controlling of Nonspecific Binding: Combination of Enzyme Amplification and Sensitive Electrochemical Detection; Analytical Science, 9:641–646 (1993).

Tanaka et al., Electrochemical Luminescense–Based Homogeneous Immunosensor Sensors and Actuators B, 13–14:184–187 (1993).

Thompson et al., Zeptomole Detection Limit for Alkaline Phosphatase Using 4–Aminophenylphosphate, Amperometric Detection, and an Optimal Buffer System, Analytica Chimica Acta, 271:223–229 (1993).

Tie et al., An Improved ELISA with Linear Sweep Voltametry Detection, Journal of Immunological MethodS, 149:115–120 (1992).

Umana, et al., Enzyme–Enhanced Electrochemical Immunoassay for Phenytoin, Journal of Research of the National Institutes of Standards and Technology, 93(6):659–661 (1988).

Wang et al., Cobalt Phthalocyanine/Cellulose Acetate Chemically Modified Electrodes for Electromechanical Detection in Flowing Streams. Multifunctional Operation Based Upon the coupling of Electrocatalysis and Permselectivity, Anal. Chem., 60(15):1643–1645 (1988).

Yan et al., Electrochemical Homogeneous Enzyme Immunoassay of Theophylline in Hemolyzed, Icteric, and Lipemic Samples, Clin. Chem., vol. 30(7):1432–1434 (1993).

Xu et al., Solid Phase Electrochemical Enzyme Immunoassay with Attomole Detection Limit by Flow Injection Analysis, Journal of Pharmaceutical & Biomedical Analysis, 7(12):1401–1311 (1989).

SmartSense™Biosensor Assay® System, National Environmental Technology Applications Corporation, VII–13 (1993).

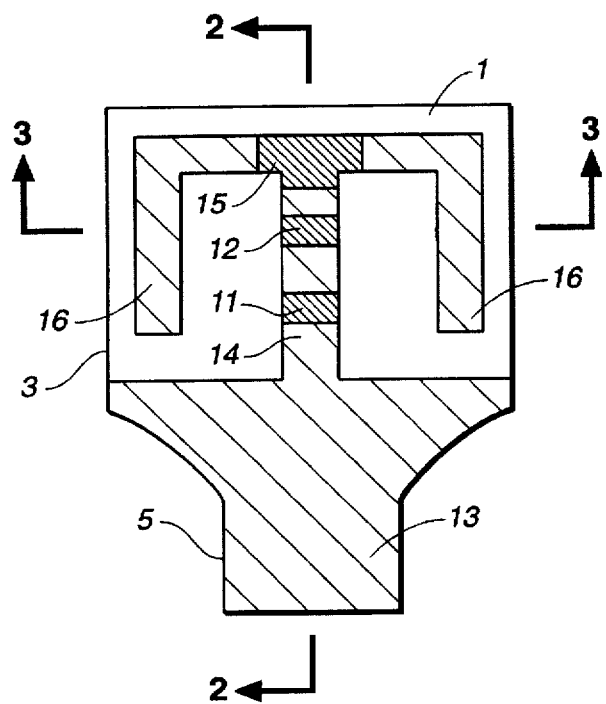
FIG._1
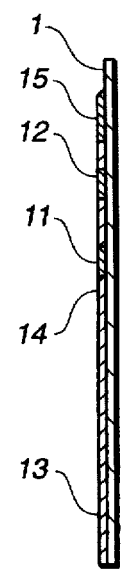
FIG._2
FIG._3
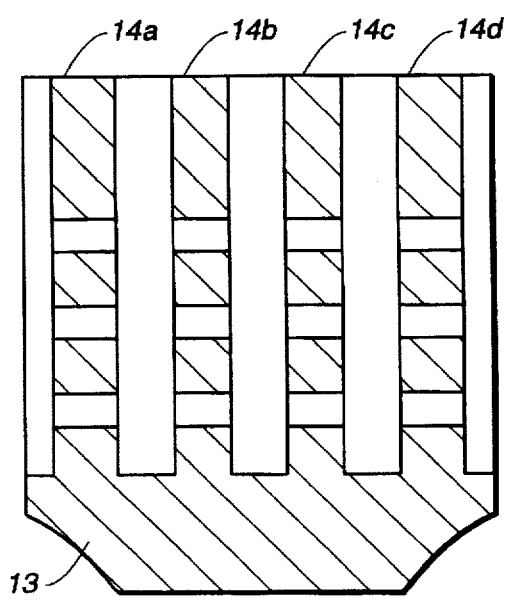
FIG._4

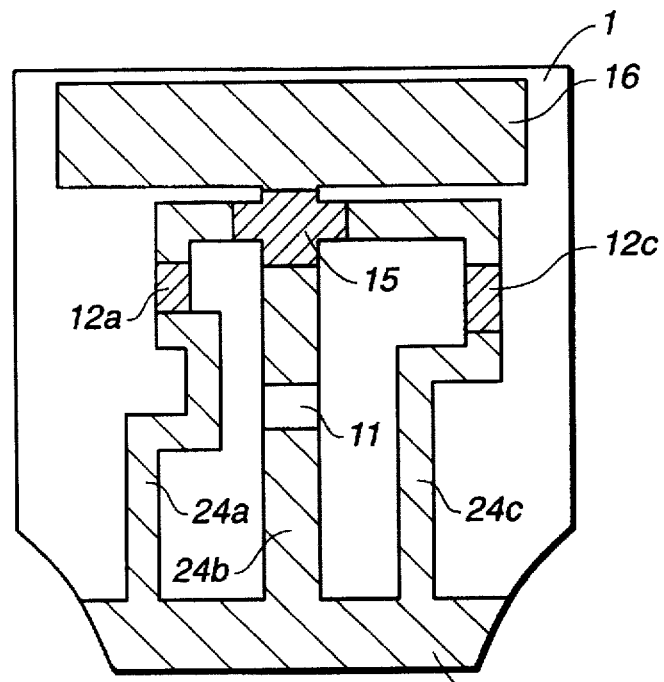
FIG._5
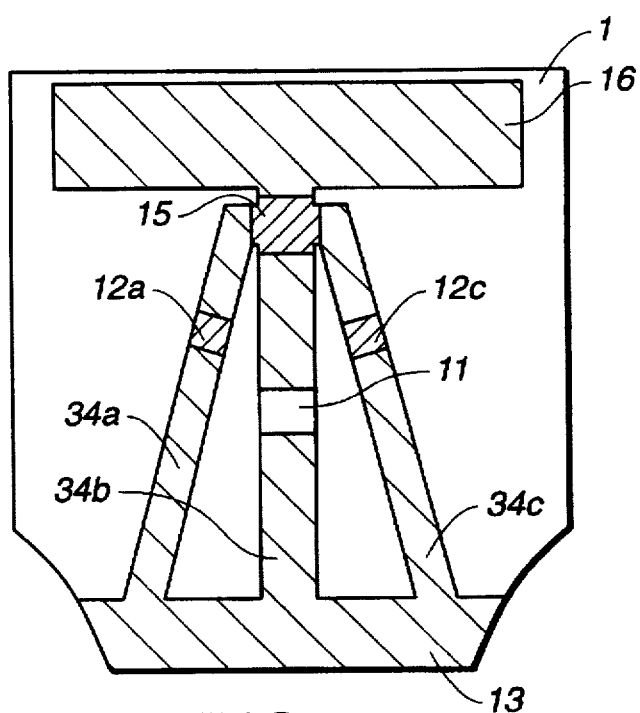
FIG._6

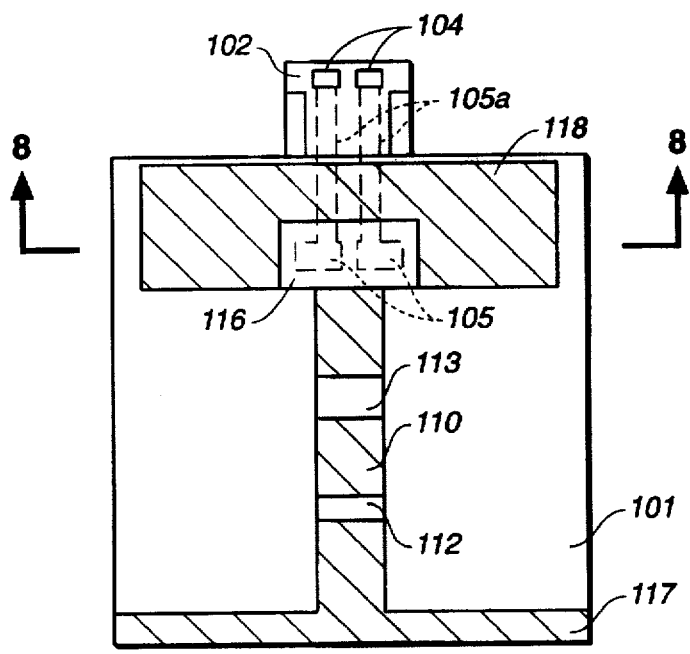
FIG._7
FIG._8
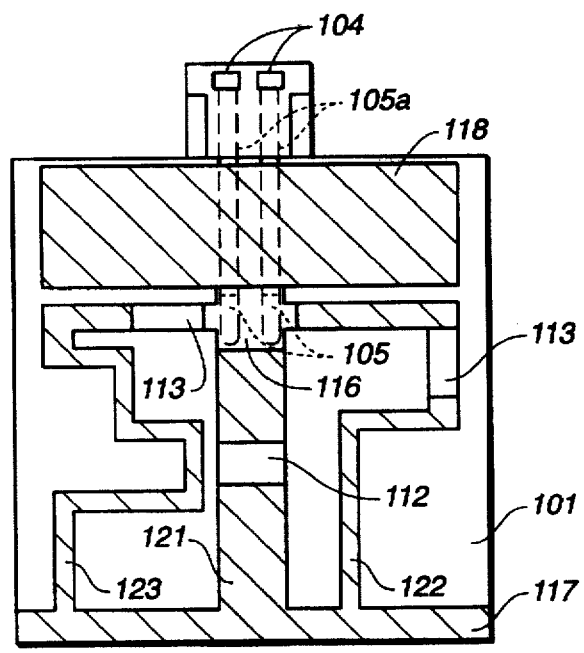
FIG._9

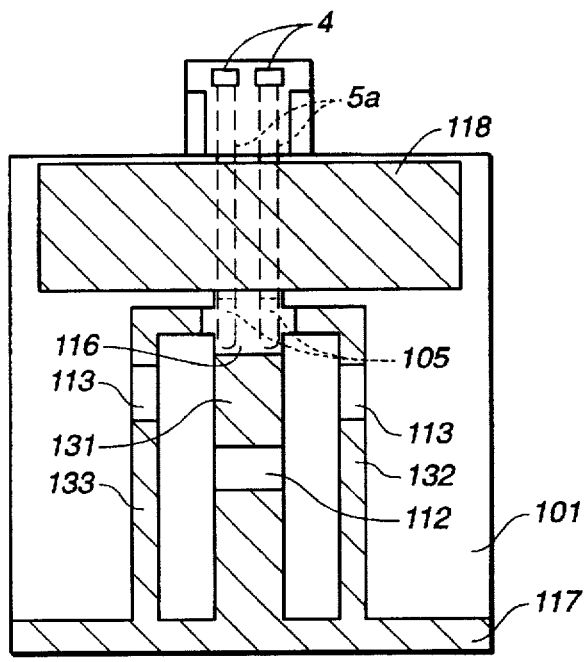
FIG._10
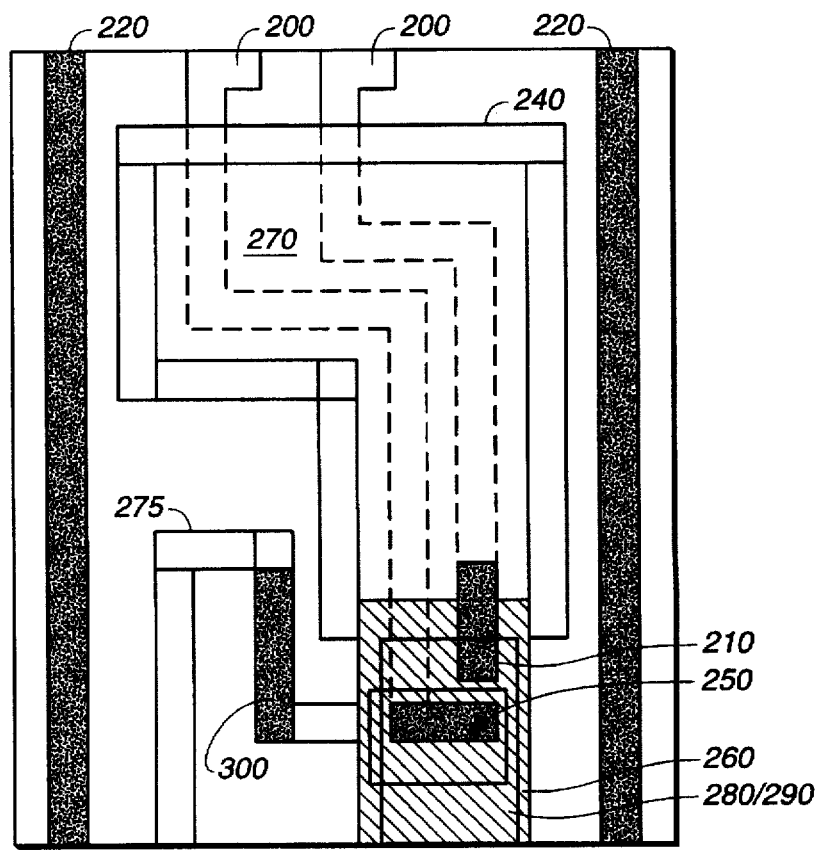
FIG._11

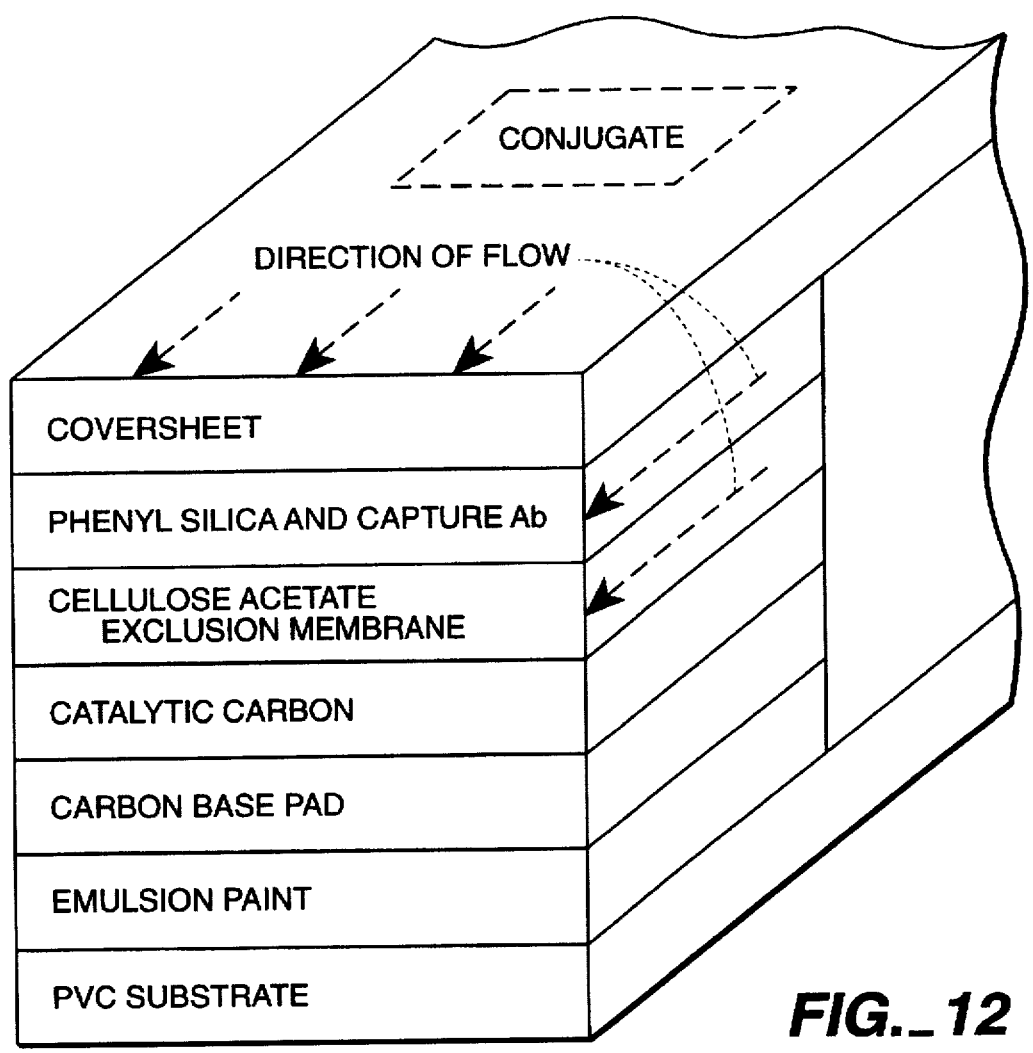
FIG._12

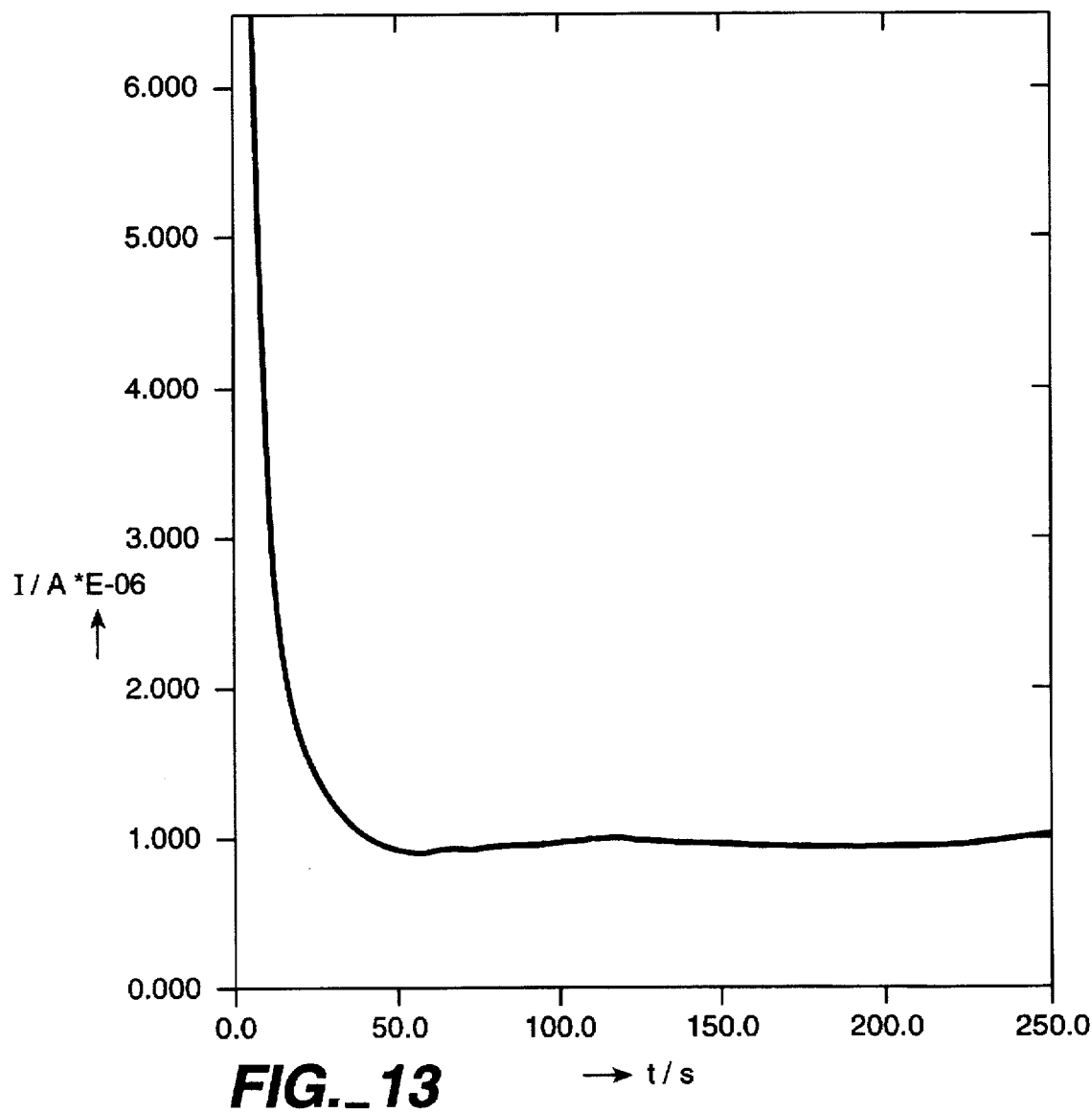
FIG._13

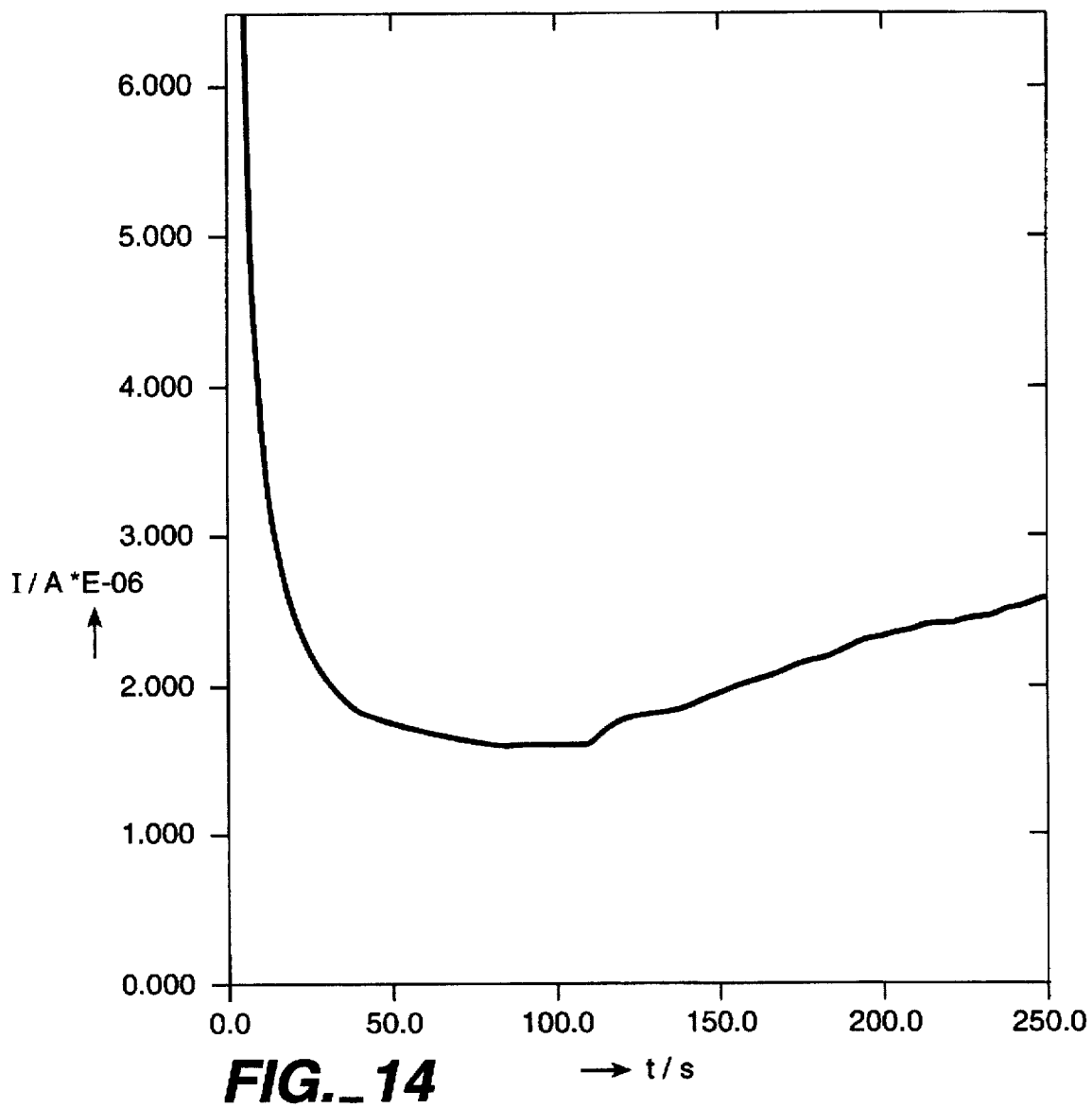
FIG._14

5,736,188

PRINTED FLUID TRANSPORT DEVICES

TECHNICAL FIELD

The present invention relates to printed fluid transport devices, compositions and methods for their manufacture, and use as assay platforms. The invention particularly relates to analytical sensor devices, e.g. for biological samples, such as electrochemical assay devices.

BACKGROUND

The development of a rapid, simple method for carrying out a range of biochemical assays would greatly enhance the field of diagnostics, particularly in areas such as the health care, environmental monitoring and food industries. For effective "on-site" use, the device should be operated with the minimum mount of manual manipulation and be suitable for use by non-specialist operators. At present the majority of assays which are performed involve several steps which are often time consuming, laborious and require technical training. Sequential additions of assay components (e.g. reactants, substrates, etc.) is an inherent feature of such assays, requiring technical skills and, in many instances, a degree of manual dexterity.

The ability to detect and monitor a number of analytes in a given sample using a single test device would facilitate an improvement in the use of such diagnostic tests.

To ameliorate the problems outlined above, devices have previously been described that utilize liquid flow channels to deliver a timed sequence of reagent additions to sample. GB-B-2 231 150 describes the use of a device comprising two flow channels leading to a common channel, all formed of a single sheet of porous material, e.g., filter paper. One of the channels is of greater length so that it delivers the liquid with a relative delay to the common channel. This allows for the sequential timed delivery of reagents, through capillary liquid flow, to a common site. It is not easy to provide elaborate systems of channels. If a long delay is required, a channel must be made very long and hence, very convoluted. This is inconvenient, and providing two or more channels with long delays tends to be impracticable. R. Bunce et al., *Anal. Chim. Acta*, 249, 263-269 (1991) disclose such devices in which pathways are delimited on a sheet of filter paper by printing hydrophobic regions into the paper using a wax-resist batik technique, so that the non-printed regions provide the pathways. Such methods are of limited practical utility in the manufacture of assay kits.

U.S. Pat. No. 5,194,133 describes a device that can be used for the analysis of a sample fluid containing a substrate. A single channel is formed by micromachining of a suitable material. Subsequently, the channel is filled with a material capable of acting as a chromatographic separation medium. Biological material can be incorporated into the chromatographic matrix, allowing controlled reactions to occur. Detection is by means of electrochemical sensors located at defined points along the channel.

W. Schramm et al., *'Biosensors '92 Proceedings'* (published by Elsevier Advanced Technology, Oxford, England) discloses an immunoassay device having a strip of chromatographic material with a detection zone with an immobilized antibody and, upstream thereof, a deposit of a reagent (analyte-enzyme conjugate). A porcelain chip has a printed electrode located in contact with the detection zone. In use, analyte solution passes up the strip and carries the reagent to the detection zone. Analyte and analyte-enzyme conjugate compete to bind to the antibody. An enzyme substrate is provided and generates an electroactive product at the detection zone. The electrode system provides a signal whose strength varies inversely with the amount of analyte in the analyte solution.

SUMMARY OF THE INVENTION

The present invention provides for a fluid transport device comprising a backing sheet and at least one fluid pathway defined by a pattern of material through which fluid can flow and printed onto the backing sheet. Such pathways can be referred to as guidance pathways that guide fluid flow parallel or perpendicular to the plane of the backing sheet. Desirably, the pathway(s) fluidly communicate with a detection zone, and the device further includes an electrode assembly which provides an electrode means disposed in relation to the detection zone to enable the detection of chemical species. Preferably, the electrode assembly is applied by a printing technique.

The guidance pathway material will typically have capillarity and be made with a bibulous material and/or a chromatographic medium.

The present invention further provides for a method of manufacturing a fluid transport device comprising providing a backing sheet and printing a material on the backing sheet that provides at least one fluid pathway. Preferably, the method comprises providing a backing sheet and, in either order, (i) applying to it by a printing technique an electrode assembly; and (ii) applying to it by a printing technique a material which provides at least one fluid pathway disposed so that a detection zone thereof overlies or underlies at least part of the electrode assembly.

BRIEF DESCRIPTION OF THE DRAWINGS

Some embodiments of the invention are further described below, by way of example, with reference to the accompanying drawings.

FIG. 1 is a plan view of an assay device which is a first embodiment.

FIG. 2 is a section of II—II in FIG. 1; FIG. 3 is a section of III—III in FIG. 1.

FIGS. 4, 5, 6 are plan views of the second, third and fourth embodiments.

FIG. 7 is a plan view of a fifth embodiment; FIG. 8 is a section on VIII—VIII in FIG. 7.

FIGS. 9 and 10 are plan views of the sixth and seventh embodiments.

FIG. 11 is a plan view of a test card.

FIG. 12 is a three dimensional cross section of a portion of a detection zone shown in FIG. 11.

FIG. 13 is a control current measured using a test card in the absence of an analyte.

FIG. 14 is a current measured using a test card in the presence of an analyte.

DESCRIPTION OF SPECIFIC EMBODIMENTS

The present invention provides for printed fluid transport devices. Such devices find application where fluid flow must be directed or timed. Printed fluid transport devices can be used as assay platforms to permit convenient and rapid measurements of analytes, as well as for the economical and efficient mass production of disposable test cards. "Test cards" refers to printed fluid flow devices that can be used for assays of analytes in fluids, particularly in small and convenient assay kits. The printed devices and techniques disclosed herein are particularly useful for the manufacture of test cards that use an electrochemical detection means, such as, but not limited to, printed electrode assemblies discussed herein.

The fluid transport devices comprise a backing sheet and at least one fluid guiding pathway defined by a pattern of material through which fluid can flow. As illustrated in the FIGS. of various embodiments of the invention, the fluid guiding pathways permit fluid to be transported from a sample application site to at least the detection zone. Typically, as illustrated in various embodiments disclosed in the FIGS., such as FIGS. 1—10, fluid transport through printed fluid guiding pathways will be parallel to the plane of the backing sheet, with minimal fluid transport perpendicular to the plane of the backing sheet. Usually, fluid transport perpendicular to the plane of the backing sheet (provided by the buffer or sample stream in the fluid guiding pathway) will be less than 10% of the fluid transport parallel to the plane of the backing sheet. Fluid transport perpendicular to the plane of the backing sheet will increase in relation to fluid transport parallel to the plane of the backing sheet in some regions of the fluid guiding pathways, such as thicker layer regions in waste zones that contain a large amount of wicking material in relation to the reagent, liquid application and detection zones.

Generally, printed fluid guiding pathways provide directional fluid transport through a printed fluid guiding pathway. Directional fluid transport relates to net transport of fluid through the material or materials forming a printed fluid guiding pathway and between at least two points along the printed fluid guiding pathway. For example, buffer enters a liquid application zone and is transported through the matrix or materials forming the printed fluid guiding pathway in a direction away from the initial site of liquid application, i.e., directional transport. Typically, printed fluid guiding pathways will provide directional fluid transport through a detection zone during detection of an analyte. In most instances, fluid transport is not stopped in the fluid detection zone. In some embodiments of the invention, such as those with certain types of flow accelerators, as discussed herein, fluid transport will be assisted by non-matrix fluid transport regions that have capillary flow parallel to, or in generally the same direction as, the fluid transport through the printed fluid guiding pathways. Many embodiments of the invention will lack non-matrix fluid transport regions. Such non-matrix fluid transport regions include those comprised of a capillary track, tube, channel or slit formed by two planar surfaces (such as glass) appropriately distanced to permit capillary flow; such non-matrix fluid transport regions are recognized by the air or gaseous gap between two surfaces that permit capillary flow of the fluid.

The printing techniques disclosed herein provide for any desired pattern of fluid guiding pathways. Generally, a defined printed pattern of a fluid guiding pathway refers to a pattern of printed material that will permit directional fluid transport. Furthermore different "inks" or "pastes" can be applied to produce fluid guiding pathways that can include fluid guiding pathway portions having different flow properties. Generally, the term paste relates to materials at a concentration of 10 to 60% (w/v) typically in water or an organic solvent. Preferably pastes are used in the 20 to 40% (w/v) range. Printing compositions usually range from 1 to 25 poise at 25° C., preferably from 4 to 18 poise at 25° C. and more preferably at 6 to 12 poise at 25° C. The term "flow properties" may refer to properties affecting liquid flow along a fluid guiding pathway or to properties affecting the conveyance of solutes by carrier liquids as in chromatography. Materials can be used to change solute/solvent RF values. RF value refers to the ratio of the distance moved by a particular solute to that moved by a solvent front. For example, printed fluid guiding pathways can be manufactured with a printed layer or layers comprised of two or more different materials ("multi-material") providing different rates of fluid transport. Multi-material fluid guiding pathways can be used when it is desirable to modify retention times of reagents in fluid guiding pathways (such as reduction of retention times, as discussed herein for conjugates, or to increase retention times to allow reactions to occur, e.g., antibody-analyte interactions), prevent non-specific binding, improve the assay sensitivity or improve the reproducibility of analyte assays. Such multi-material fluid guiding pathways can be constructed as a heterogenous printed layer, where a plurality of materials are mixed together and then printed. Multi-material fluid guiding pathways can be also made by printing multiple layers of materials with different flow properties on top of one another. Multi-material fluid guiding pathways are examples of some types of flow accelerators further described herein.

Printed fluid guiding pathways can be provided with regions containing reagent substances, by including reagent substances in the "inks" used to produce them or by a subsequent printing step. A preferred printing technique to use is screen printing. Such regions are usually referred to as reagent zones. Non-immobilized reagents are preferably printed on materials that release the reagents quickly to the fluid flow to allow for rapid hydration of reagents and less reagent retention. Inert materials are especially suitable for this purpose.

Screen printing techniques are also preferably used for printing fluid guiding pathways, conductivity strips, electrodes and their associated conduction tracks, and for printing reagents at specific fluid guiding pathway locations. Air-brushing may also be used to print fluid guiding pathways. Ink jet printing can be used for printing reagents but is not generally suitable for depositing particulate material greater than 20–5μ.

The present invention makes available an improved technique of controlling the flow of liquid and the subsequent timing of reagent delivery in an assay device. Geometrically defined and printed fluid guiding pathways can be used to guide the fluid flow and can be made of disparate chromatographic materials (such as cellulose, silica gel, silica including silica modified to increase the hydrophobicity of the silica, starch, agarose, alginate, carrageenin or polyacrylic polymer gel and mixtures of such materials) to facilitate appropriate retention of individual reagents and to assist and enhance the sequential delivery of the assay components. Different physical, as well as chemical, properties can be used to affect transit times, e.g., densely packed small particles produce longer transit times than loosely packed larger particles of the same material. Regularly shaped particles can be deposited to form a closely packed regular structure which facilitates the passage of proteinaceous material.

Generally, printed fluid guiding pathways, especially screened printed fluid pathways, comprise thin layers of matrix sufficiently thick so as to provide enough fluid for a detectable signal and to ensure uniformity. Typically, a single printed layer can vary from 5 to 500μ in thickness and preferably, 5 to 100μ or 40 to 100μ in thickness and more preferably 40 to 100μ in thickness. Fluid guiding pathways can be made of multiple layers or single layers wherein the total layer thickness is usually 50 to 500μ and preferably, 75 to 300μ.

"Silica" includes silica derivatives, which can be selected to meet the requirements of a particular assay. The average silica particle for printed fluid guiding pathways usually ranges from 2µ to 100µ and preferably, 5µ to 25µ or 10µ to 50µ. For example, there are commercially available silica-bearing groups to which components can be immobilized, such as silicas with hydrophobic groups, particularly phenyl, benzyl, two aromatic rings and substituted phenyls, as well as ODS2-Silica (5µ) and Spherisorb S5-Epoxide (both from Phase Separations). Phenyl silica generally refers to a phenol group attached a silane group via a short carbon linkage, preferably, 1 to 4 carbons in length and more preferably, by a single carbon. Phenyl silica is preferred for printing fluid guiding pathways leading up to or adjacent to the detection zone, and more preferably, phenyl silica with an average particle size of 5µ is used. Generally, the role of silicas with hydrophobic groups, such as phenyl silica, is to act an immobilization matrix for reagents, such as a capture antibody, and as a matrix that has a minimum of non-specific conjugate binding when blocked.

Derivatized silica is typically used with a cellulose derivative for printing compositions. A silica paste is made with a solvent at a concentration of 10 to 60% (w/v) and preferably, 40 to 60% (w/v). Often the solvent is water. Other solvents can be used such as methanol, ethanol, propanol, butanol, 2-butoxyethyl acetate (99%) and 1-(2-ethoxyethoxy) ethyl ester, either individually or in combination. Pastes from silica with hydrophobic groups such, as phenyl silica pastes, are preferred. The cellulose derivative mixed with the silica paste is preferably hydroxyethylcellulose and typically mixed at a ratio of 0.2:1 to 3:1 ratio (w/w of paste to hydroxyethylcellulose solution), preferably, 0.5:1 to 2:1 (w/w) and more preferably, 1:1 (w/w). Hydroxyethylcellulose solutions are typically aqueous-based, but other solvents as known in the art can be used, so long as they are compatible with the printing process of choice. Hydroxyethylcellulose solutions are typically 1 to 25% (w/v), preferably 5 to 15% and more preferably, 9 to 11%. Calcium phosphate is the preferred binder, although calcium sulphate, gelatine and other binders as known in the art can be used. Typically, binder concentrations are 5 to 40% (w/w) with a preferred concentration of 8 to 14% and a most preferred concentration of 12.5% (w/w). Microwaving can be used to enhance homogenization of the paste. Such derivatized silicas can be blocked with blocking materials as described herein and taught in the art. Proteins can be immobilized on dervatized silicas, particularly phenyl and epoxide silicas, such as proteins required for the assays described herein and known in the art. For example, capture antibodies, other capture ligands or a member of a receptor pair can be immobilized.

"Cellulose" includes cellulose derivatives. For example, nitroeellulose may be used to provide a pathway portion that tends to retard (polar) solutes, while fibrous cellulose may be used to give rapid flow. Variations in nitro-cellulose flow properties are well-known in the field of chromatography. Cellulose acetate is particularly useful for exclusion membranes, as discussed herein. Cellulose acetate usually has an acetyl content of 20 to 90%, and preferably 30 to 50%.

Using printing techniques such as screen printing, well-defined, complex and reproducible pathway patterns can be laid down on an inert backing material. Porous material can be deposited in layers, by successive printing steps, to achieve desired pathway thickness for desired flow rates. A thicker pathway portion tends to exhibit a lower flow rate. Different fluid guiding pathways and/or different portions of fluid guiding pathways can differ in thickness dependent on, for instance, the desired timing of solutes at a merged zone.

For screen printing, screens are as selected in relation to the size and viscosity of the particulate composition being printed. Low viscosity generally requires higher counts per inch for uniform printing of layers. For pastes, larger mesh size (i.e., low-count per inch) screens are usually better. Generally, screen hole size is 2 to 3 times larger than the average particle size being printed. Screens are often coated with an emulsion to protect them from the solvents used in the printing compositions.

A backing sheet may comprise thin plastics material, e.g., PVC (Polyvinyl Chloride) sheet. Backing sheets can be provided with a more polar or hydrophilic coating to enhance the adhesion of the fluid guidance pathway material. A resin composition loaded with carbon (e.g., Electrorag 423SS graphite-based polymer thick film ink, Acheson Colloid Co., Plymouth, GB) may be used to coat backing sheets not relying on electrochemical detection. A conventional emulsion paint may be generally suitable for both electrochemical and non-electrochemical devices, such as Dulux or other emulsion paints known in the art. An emulsion paint is a water-thinnable paint made from an emulsion or dispersion of a resin (generally synthetic) in water. The resin may be polyvinyl chloride, an acrylic resin or the like. Other backing sheets, e.g., of glass or other ceramic material, may not require coatings. Backing sheet materials include polyurethane, polyester, polycarbonate, polycarbonate/polyester blends and polyalkylenes, either singly or in combinations thereof. Titanium oxides can be blended with such materials to improve performance characteristics, U.S. Pat. No. 5,238,737, the methods of which are herein incorporated by reference.

For electrodes, a variety of electrode assemblies can be used, including two- and three-electrode-based assemblies. Two-electrode assemblies are preferred because of the ease of operation and printing of the electrodes and conduction tracks. Working electrodes are preferably catalyzed carbon based, such as rhodinized carbon electrodes like MCA 4 (MCA, Cambridge, United Kingdom). Other electrodes based on a combination of carbon and transition metals, preferably platinium, can be used to facilitate low potential oxidation of enzyme product. Such electrodes help reduce background noise associated with measuring assay products, such as $H_2O_2$, at higher voltages (600–700mV versus Ag/AgCl reference electrode) required by other types of electrodes, e.g., pure carbon or pure platium group based electrodes. Generally, it is advantageous to incorporate in a two-electrode system an auxiliary/reference of sufficient size so as not to limit the current required for the potentiostat. For reference electrodes, Ag/AgCl is typically used in the range of 10 to 90% Ag, although for disposable test cards, 10% is preferable. Electrodes are preferably printed so as to maximize detection, for instance by locating the electrode broadside to the fluid transport, as well as creating an interdigitating pattern between the reference and working electrodes.

Conducting polymers in the form of a layer or film can be used in conjunction with the printed electrode assemblies. Usually, the conducting polymer is a heteroaromatie conducting polymer, like a polypyrrole, a poly(thienylene vinylerie), a poly(furylene vinylene), a polyfuran or a polythiophene. Mediator compounds can also be used with printed electrode assemblies, such as, but not limited to, ferrocenes, ferrocene derivatives, non-ferrocene mediators (e.g., carbon-boron compounds (including the carboranes)), Viologens (N,N'-dialkyl of or diaryl derivatives of 4,4'- bipyridyl), one-dimensional conductors (including the salts of TCNQ), phenazine dyes (including phenazine methosulphate and phenazine ethosulphate) and metalloporphyrins (including cytochrome-C) and transition metal complexes, particularly those in which the mediator comprises at least one or two organic rings.

For conduction tracks, Ag is typically used in printing compositions. The size of these tracks is minimized to reduce noise created by increase surface area. Typically, such tracks are shrouded by insulation material, which is often coated or in many cases, printed. Insulation material is usually a matt vinyl emulsion paint. Other insulation and conductive track materials may be used and known in the art, so long as they can be adapted for use in printing compositions described, especially for screen printing.

Conductivity strips can be used with test cards described herein to trigger electrode monitoring of a reaction product. Typically, conductivity strips are printed along the length of the test card and made from a graphite-based ink.

The methods of manufacture disclosed herein are applicable to the mass production of devices. Universal test cards designs are permitted because printing screens with universal patterns can be used for a myriad of different assays by simply changing the reagents, and possibly the electrodes, but without changing the pattern of the fluid guiding pathways. The test card design may also be varied as required, by simply substituting alternative screens for appropriate parts of the production process. Printing techniques are universally applicable to the deposition (in precise locations) on the fluid guiding pathways of reagents such as: biological material(s) (e.g., antibody, labelled antibody, antigen, labelled antigen, antibody fragment, enzyme, cell receptor, intact cell or nucleic acid), electrochemically active compound(s) e.g., mediators such as ferrocene, tetrathiafulvalene and Meldola blue) and necessary unlabelled or labelled substrate(s), e.g., glucose.

The detection zone can be made to accommodate a variety of optical detection methods, including visual, flourometric, colormetric, reflective, densimetric and those methods based on absorbance and transmittance. The assay techniques discussed herein and known in the art can be combined with the use of printed fluid guiding pathways to optically measure many types of analytes, including those discussed herein, including organisms, cells, proteins and small molecules, such as therapeutic drugs, drugs of substance abuse, steroids, and naturally occurring hormones. For many optical methods, such as visually based assays, printed fluid guiding pathways can be used in detection zones to locate reaction products for easy detection. For example, the capture moiety of a capture assay can be immobilized in the detection zone to allow detection of a precipitable reaction product, such as a colored product. For assays based on the absorbance or fluorescence spectra (or amplitude at a particular wavelength) of a chemical species, the detection zone can provide for transparent windows in the backing sheets that permit light to be transmitted or focused through the backing sheet and the fluid being transported. Such windows optionally lack materials used for the printed fluid pathway. If materials for a printed fluid pathway are printed over the window area, such materials should be transparent. Alternatively, fluid guiding pathways can be printed to form a series of tracks with windows between each track and the tracks being appropriately distanced to permit capillary contact between the tracks and fluid movement across the windows. Light scatter from the tracks can be subtracted out as background noise prior to the monitoring of an optical signal generated by a chemical species. Spectral analysis of signal that passes through the window or windows will be particularly useful for identifying an optical signal related to a chemical species.

Optical assemblies described herein can be combined with assays described herein and known in the art. Optical assays are preferably used with the following assay components 1) an antibody or analyte binding moiety linked to a color change component, such as horse radish peroxidase (peroxidase) (using e.g. 3, 3', 5, 5' tetramethylbenzidine (TMB), 2, 2"azinobis (e-ethyl benzothioline-6-sulphonic acid) diammonium salt (ABTS), ortho-phenylenediamine (OPD), 4-chloro-1-napthol (4-CN), 3, 3'-dianinobenzidine tetrahydrochloride (DAB), or 3 amino 9-ethyl carbazol (AEC)); alkaline phosphatase (using e.g. para-nitrophenyl phosphate, di-sodium salt (PNP), nitro blue tetrazolium chloride (NBT), 5-bromo-4-chloro-3'-indolyphosphate paratoluidine (BCIP), iodonitrtotrazolium violet, NADP, diaphorase red (formazan), phenolpthalein monophosphate red, or fast red, napthol AS-MX phosphate)); $\beta$-galactosidase (using e.g. ortho-nitrophenyl-B-D-galactopyranoside, 5-bromo-4-chloro-3-indolyl galactopyranoside); glucose oxidase (using e.g. glucose, peroxidase, ortho-dianisine hydrochloride ($H_2O_2$ generated converted by HRP), and quineimine; glucose, peroxidase, 3, 3, 5, 5-tetramethyl benzidine (TMP) ($H_2O_2$ generated converted by HRP); urease (using e.g. urea, hypochlorite and phenol (Bertholat reaction generates ammonia) (indopohenol)); creatine kinase (using e.g. creatinin and ATP); cholesterol oxidase (using e.g. cholesterol color change formation of cholesterol 4-en 3-one); lactate monoxygenase (using e.g. lactate); lactate dehydrogenase (using e.g. lactate and AND); uricase (using e.g. uric acid); realate dehydrogenase (using e.g. realate, oxaolacetate, and NAD as cofactor); 2) luminescence components luciferase (using e.g. luciferin and ATP); peroxidase (using e.g. luminol (cyclic diacyl hydrazide)); alkaline phosphatase; cholesterol oxidase; glucose oxidase, $\beta$-galactosidase, and intertase, either individually or a suitable combination thereof. Optical components generating $H_2O_2$ can also be used for the electrical assemblies discussed herein.

Assays related to the health care field can be performed using the methods, compositions and devices described herein. Such assays include assays for: 1) pathogens such as HIV, hepatitis A, B and C virus, tuberculosis, chlamydia, gonorrhea, brachematis, protein marker for Alzheimer's disease, *Neisseria gonorrhoea*, *Vibrio cholerae*, syphilis (*Treponema pallidum*), Herpes viruses, human papilloma virus, tuberculosis (*Mycobacterium tuberculosis*), and group A strep; 2) surface antigens of pathogens; 3) antibodies of pathogens (ie. serological assays); 4) therapeutic drugs such as theophyilline, digoxin, caffeine, theophylline, amikacin, gentamicin, netilmicin, tobramycin, vancomycin, carbamazepine, phenobarbital, phenytoin, primidone, valproic acid, digoxin, disopyramide, lidocaine, N-acetylprocainamide, procainamide, quinidine, amitriptyline, nortriptyline, imipramine, desipramine, cyclosporine, acetaminophen, chloramphenicol, and methotrexate, 5) abused substances such as barbiturates, benzodiazepines, cannabinoids, cocaine metabolics, methaqualone, opiates, methadone, phencyclidiine, amphetamine and methamphetamine, 6) therapeutic drug monitoring for drugs such as theophylline, lidocaine, disopyramide, N-acetylprocainamide, procainamide, quinidine, flecainide, amikacin, gentamicin, kanamycin, neitilmicin, streptomycin, tobramycin, vancomycin, carhamazepine, phenytoin, phenobarbital, primidone, valproic acid, ethosuximide, methotrexate, digoxin, digiton, and cyclosporin, and 7) other analytes such as hCG, LH, β-inhibin, thyroxine and bilirubin.

Assays related to the food, veterinary and environmental fields can be performed using the methods, compositions and devices described herein. Such assays include assays for: 1) pesticides and compounds such as dioxins, dibenzofurans, PCB's, triazine, aldrin, alachlor, atrazine, bacillus thuringensis toxin, BAY SIR 8514, S-bioallethin, chlorosulfuron, cyanzine, 2,4-D, DDT, dichlorfop-methyl, dieldrin, difubenzuron, endosulfon, iprodione, kepone, malete hydrazide, metalaxyl, oxfendazole, parathlon, panoxon, paraquat, pentachlorophenol, 2,4,5-T, terhutryn, triadimefon, and warfarin; 2) livestock diseases such as *Taxoplasma gondii, Brucella abortus, Stephanuras dentatus, Mycoplasma bovis*, Bovine rhinotracheitis, Maedi visna virus, swine fever virus, *Leptospira interrogans*, and coronavirus; 3) anabolic agents such as 17β-estradiol, estrogen, testosterone, 17α-methyltestosterone, progesterone, trenbolone, diethylstilbestrol, hexoestrol, and zeronat; 4) toxins and pathogens such as *Clostridium botulinum* neurotoxin A, B, E, F, G, *Staphylococcus aureus*, enterotoxins A, B, C, D, E, Aflatoxins B1, B2, B4 diol, M1, Q1, Ochratoxin, T-2 toxin, 3'-OH-T-2 toxin, T-2 tetranltetracetate, HT-2 toxin, group A trichothecenes, roridin A, diacetoxyscirpenol, deoxynlvalonel, 3-Acetyl deoxynivalenol, deoxyverrucarol, zearalenone, sterigmatocystin, rubratoxin B, PR toxin, Salmonella, *Listeria monocytogenes, Escherichia coli*, Vibrae epp., *Yersinia enterocolitica*, and *Campylobacter jejuni*.

Assays related to the defense fields can be performed using the methods, compositions and devices described herein. Such assays include Anthrax spores (*Bacillus anthracis*), Ebola virus, *Staphylococus aurens* enterofixin B (& others), Yellow fever virus, cloned protein toxins (eg. snake, scorpion), Lassa fever virus, and Ricin, Yersuia pestis.

Cholesterol is preferably measured using cholesterol oxidase/$H_2O_2$ assay system using $H_2O_2$ sensing electrodes, preferably containing palladium or metal chelated substances, such as, but not limited to, cobalt phthalocyanine' Gilmartin et al., *Analyst*, 119:2331–2336 (1994), the methods of which are herein incorporated by reference; and Dong et al., Ana. Chim. Acta, 279:235–240 (1993), the methods of which are herein incorporated by reference. Such electrode methods can also be combined with other assays described herein.

In general, a device embodying the invention has a detection zone where the applied analyte produces, directly or indirectly, a detectable phenomenon, e.g., relating to the production of color, suppression of production of color or the generation (or the suppression of generation) of a species that is detectable electrochemically. Often, the detection zone is located downstream of a merged zone, where two or more fluid guiding pathways merge to form one fluid guiding pathway. The detection zone may have means for tending to retain, or reduce the loss of, species responsible for the detectable phenomenon. Thus, where a detection zone extends over only a part of the width of a pathway, it may be delimited at one or both sides by barriers to lateral diffusion.

A trapping zone can also be provided in the region of the detection zone. This could be a charged layer which would serve the purpose of concentrating oppositely charged species at the detection zone, e.g., Nafion is a suitable negatively charged membrane material. Alternatively, a material chosen on basis of size exclusion could be used, e.g., cellulose acetate.

For example a device based on the generation of hydrogen peroxide and its electrochemical detection could have a trapping layer in the region of the detection electrodes which is adapted to retain hydrogen peroxide.

A device based on the generation of a reduced mediator (e.g., hexacyanoferrate) may have a trapping layer that retains the mediator by charge attraction.

Exclusion membrane can protect against fouling of the electrode surface and can be made from polyurethane as well.

Incomplete removal of unbound antibody conjugate from the electrode site can affect the performance of the electrode assembly. Unbound antibody conjugate adhering to the carbon surface of an electrode or matrix surrounding an electrode assembly can lead to erroneous signals. This can occur if the "wicking power" of matrix, such as silica, particularly phenyl silica, is insufficient to remove unbound conjugate. Experiments involving the deposition of protein conjugate directly onto the surface of the bare, carbon-based electrodes, followed by extensive washing with water (using a wash bottle), revealed binding between protein conjugate and the electrode surface.

Decrease in the performance of the electrode system due to unbound conjugate can be overcome by 1) the use of blocking materials to cover potential binding sites on and around the electrode(s) and 2) the use of a size selective membrane over the electrode that enables a reaction product, such as an enzyme product, for instance, $H_2O_2$, to pass through to the electrode surface while preventing the binding of unbound conjugate to the electrode.

For blocking materials BSA, casein, goat serum and skimmed milk, as well as other blocking materials known in the art, can be used, as long as those materials do not interfere with electrode measurement. Preferably, blocking materials are used that mimic or are derived from a source similar to either the sample being tested or the antibodies used in the assay or a combination thereof. Interference is easily tested by applying varying amounts of the candidate blocking material to the electrode assembly and monitoring the electrode assembly's sensitivity after successive washes. If blocking materials diminish the electrical signal, the concentrations can be lowered even to zero, and a protective or exclusion membrane can then be used to reduce the affect of non-specific binding. Typically, the electrode structure is printed before the primary capture antibody is immobilized on to the silica which forms a layer directly over the electrode's carbon surface. Following immobilization, the silica, such as phenyl silica, is blocked with either one or several of the blocking materials, which are usually in the 1% to 10% concentration range (w/v).

For a size-selective exclusion membrane, various materials can be used such as cellulose acetate, porous polypropylene, porous nylon, porous polycarbonate, porous polyurethane, silicon-containing elastomers and similar porous material, either singly or in combinations. Cellulose acetate is preferred for exclusion membranes. The resulting pore size of the exclusion membrane printed using most materials, such as cellulose materials, particularly cellulose acetate, is dependent on the volatility of the solvent. Less volatile solvents, in general, lead to small pore sizes. Cyclohexanone is particularly well-suited as a solvent for cellulose acetate. To avoid slow evaporation of comparatively low-volatility solvents, such as cyclohexanone, and the consequently produced membranes with very small ill-defined pore sizes, higher-volatility solvents, such as acetone, can be mixed with the lower-volatility solvents to achieve the desired pore sizes of membranes. Mixing of high- and low-volatility solvents also improves the "printability" of solutions compared to the use of high-volatility solvents alone. Generally, cellulose acetate concentrations from 3% to 10% (w/v) can be used with varying mixtures of cyclohexanone and acetone, such as 9:1, 2:1, 1:1 and 0.5:1 (v/v), respectively. The cyclohexanone to acetone ratio (v/v) is preferably 0.5:1 to 2:1 and more preferably, 1:1. The cellulose acetate concentration is preferably 3.5 to 8% (w/v) and more preferably, 4 to 5%. Other organic solvents can be used, especially when the solvent of lower volatility has a boiling point from 100 to 175°C. and the solvent of higher volatility has a boiling point from 45 to 65°C., and the lower volatility and higher volatility solvent are mixed in at least a 0.25:1 ratio, respectively. Preferably, 4% (w/v) cellulose acetate in a mixture of high- and low-volatility solvent is used and preferably, a 1:1 (v/v) mixture of acetone and cyclohexanone is used to form an exclusion membrane. The acetyl content of the cellulose acetate is preferably at least 40 %. Such solutions are suitable for screen-printing, giving a reproducible exclusion membrane over the electrode area. This technique can also be applied to exclude other assay reagents or sample constituents from the electrodes, such as cell fragments or high molecular weight proteins.

Retention of undesired reagents in guidance pathway matrices can be reduced using flow accelerators. Flow accelerators are generally of two types: 1) material added to the printed guidance pathway printing solutions to increase fluid flow in the guidance pathway matrices or matrix, especially in the region of a dried reagent or 2) a non-matrix deposit of a dried reagent in capillary contact with the matrix or matrices of a printed guidance pathway. Such flow accelerators are particularly useful additions to the guidance pathway when retention of reagents in the guidance pathways, such as conjugates, generates a signal large enough to interfere with the detection of the signal in the presence of an analyte. For example, faster flow of conjugate through or around a matrix, particularly a phenyl silica matrix, can enhance the performance of the electrical measurement in the presence and absence of an analyte, i.e., lower backgrounds are produced, the signal-to-noise ratio can be enhanced and the reproducibility of the assay can be improved. In the case of some matrices such as silica, particularly phenyl silica, dry depositing a reagent onto the matrix can lead to incomplete hydration of reagents, such as a conjugate, by the moving buffer or sample fluid front, leading to a significant proportion of conjugate being retained and slowly released from a reservoir or reagent zone.

To improve the flow and release of a reagent to the hydrated realfix of a printed guidance pathway, reagents such as conjugates, are separately printed or deposited using non-printing techniques on the surface of a cover-sheet which is in capillary contact with the printed guidance pathway. Typically, capillary contact will arise from the placement of a cover-sheet in immediate apposition to the guidance pathway. Cover-sheets can be coated or printed with a matrix, such as a synthetic sponge to act as a quick-release reservoir of the dried reagent. Reagent can be mixed with the matrix or dried directly on the matrix or on the surface of the cover-sheet material. For all the cover-sheet embodiments discussed herein, it is preferred to locate the cover-sheet so as to optimize flow through the guidance pathway from the application site through the detection zone. Materials that improve hydration of reagents include materials such as, but not limited to, gelatin, silk fibroins, chitosan, collagen and polyacrylamid, or combinations thereof and preferably, gelatin, chitosan or silk fibroins, or combinations thereof. Printed fluid guiding pathway materials can also be mixed with at least one surfactant to improve matrix wetting, especially when multiple matrix materials are used. Such surfactants include alkanesulfonates of 5-7 carbon atoms, Tween 20, hexane sulfonate (preferably), Surfynol (tetramethyldecynediol ethoxylated with 30 moles of ethylene oxide), Triton (octyl phenoxy polyethoxy ethanol), Sitwet (polyalkyleneoxide modified dimethylsiloxanes) and short chain alkanesulfonates, such as methanesulfonate or propanesulfonate or longer chain alkanesulfonates, such as those containing from 8-10 carbon atoms.

Capillary contact with the printed guidance pathway can be also established by placing reagents on strips or islands that lack matrices. Reagents can be directly applied, on backing sheets, particularly PVC or coated PVC backing sheets, as strips or islands. Such islands or strips are preferably placed in the printed fluid guiding pathway. Alternatively, a capillary conductive hole can be designed in the backing strip, with an optionally placed, inert wicking material (e.g., a sponge) inside the hole, to provide for a reagent. Such strips, holes or islands act as a quick-release reagent reservoir that is triggered by the flow of fluid through the surrounding or adjacent guidance pathway to permit hydration of the reagent. Preferably, such reagent islands are triangle shaped, with the angle of least degrees forming the point of the triangle that first contacts fluid flow. The term cover-sheet when used without reference to covering or being located over a guidance pathway, includes such strips and islands as discussed herein. A cover-sheet may be applied to ensure fluid flow across the dried reagent.

To improve the flow or release of a reagent to the hydrated matrix of a printed guidance pathway, reagents, such as conjugates and guidance pathways, are provided that are a mixture of fast and slow transporting matrices. Fast transporting matrices can be added to the guidance pathway inks to make a printed guidance pathway to accelerate the flow of slow-moving reagents that decrease the electrical signal to noise ratio.

The first embodiment, shown in FIGS. 1–3, has a PVC backing sheet 1 shaped to provide a generally rectangular main portion 3, narrowing to a liquid application stem or zone 5. One face of the sheet 1 has a pattern of chromatographic medium (e.g., silica or cellulose) which has been applied by screen-printing a slurry of particles of the medium, followed by evaporation of the solvent, leaving a porous deposit. This pattern provides an immersion area or zone 13 which covers the stem 5 and a single fluid guiding pathway 14 that extends from the immersion area 13. Its far end is of increased area to provide a fluid reservoir or zone. In this example, it is branched, having two reservoir arms 16. The width and length of the pathway will be selected to give the maximum advantage for carrying out the assay. If necessary, the pathway can be overlaid with additional slurry of the porous material to increase the thickness and hence, the retention of reagents. Indicated on the pathway is a spotting point 11 where a known volume of sample is to be deposited. Also shown on the pathway is a dry reservoir site or zone 12 for the deposition of other components of the assay (e.g., reagents or substrates). Several such sites could be included per pathway in a typical device, e.g. applied by screen printing.

In use, the stem 5 is immersed in a buffer solution, held in a separate or integral container. The buffer will flow along the pathway by means of capillary force and chromatographic force. In doing so, the other components of the assay will be taken up and carried from the dry reservoir by the flowing liquid. Eventually, the liquid front will reach the detection area where the reaction can be monitored.

One example of the use of such a device would be for an enzyme-linked immunoassay. The assay could be based on the use of a "capture immunoassay" involving labelled antigem Enzyme-labelled antigen would be complexed with a suitable antibody, immobilized at a dry reservoir site 12. A suitable substrate for the enzyme reaction would be deposited over the detection area or zone 15. A product of the enzyme reaction is subsequently detected e.g., by a color change, electrochemical signal or an emission of light.

In a typical use of this device, a known volume of liquid sample (e.g., urine) would be applied to the spotting point 11. The stem end of the device would then be immersed in the buffer solution. As the fluid is guided up the pathway, the sample solution will pass over the dry reservoir site. Antigen present in the sample solution will displace the bound labelled antigen from the immobilized antibodies. The released labelled antigen will be carried in the buffer and guided by the pathway to the detection area where a reaction will occur with the substrate. For example, when using a colorimetric substrate in the presence of this substrate, an insoluble color will be produced, and the intensity of this color will be determined by the concentration of labelled antigen present. A sample containing a high concentration of the desired analyte will produce a more intense color. Waste reservoirs are sited behind the detection area to allow the capillary flow to continue and complete the assay.

FIG. 4 is a further extension to this approach, whereby the presence of two or more fluid pathways allows multianalysis to be carried out. Analyte assays mentioned herein, and known in the art, can be used in combination with this type of test card design. It depicts the use of four fluid guiding pathways 14 a,b,c,d extending from the immersion area 13. This is an arbitrary number and any number or combination of fluid guiding pathways could be employed with this device. Test solutions of a known volume, which may or may not be aliquots from an individual sample, are spotted at the appropriate site on each of the fluid guiding pathways. Alternatively, the test solution, such as a sample, can be applied at a single liquid application that leads to multiple fluid guiding pathways for multiple analysis. The test solutions are guided over the dry reagent reservoirs to the detection areas. Each sample is monitored independently. By selecting the appropriate pathway material and the geometric shape of the individual fluid guiding pathways, the assay can be tailored to suit the requirement of each analyte monitoring system. Beyond the detection areas, a common or individual waste reservoir system will be deposited. Flow stops when the respective reservoir is saturated and the reactions are completed. Therefore, the area, material, depth and composition of this reservoir will affect the successful operation of each of the individual assays.

FIGS. 5 and 6 illustrate a further refinement of this invention. With this approach, a single assay is performed using two or more fluid pathways. This allows for a sequential, timed delivery of a range of assay components to a single site (the detection area). Each pathway can be constructed using a selected material or materials and defined geometry and thickness (or thicknesses). Hence, the fluid flow and the retention of individual assay components can be effectively controlled.

FIGS. 5 and 6 show devices having three fluid guiding pathways 24a,b,c/34a,b,c leading from the immersion area 13 and coalescing at the detection area or zone that is also a merged zone 15. Beyond this, there is a reservoir 16. In both examples, the central pathway 24b/34b has a spotting point 11 for a sample, and the outer fluid guiding pathways have dry reagent reservoirs 12a, 12c. Furthermore, the fluid guiding pathways are such that liquid passes along all three fluid guiding pathways from the immersion area 13 towards the reservoir 16. Flow along the central pathway 24b/34b will convey sample from the spotting point 11 to the detection area 15 some time before reagent reaches that area from one outer pathway, and reagent from the other outer pathway arrives after a further delay. In FIG. 5, this sequential delivery is achieved by making the three fluid guiding pathways differ in length. In FIG. 6, the outer fluid guiding pathways are equal in length and similar in length to the central pathway, but they differ in composition, at least in part (particularly, all or part of the pathway portions downstream of the dry reagent reservoirs should permit fast flow relative to upstream of the reservoirs 12 a,c). Thus, the outer fluid guiding pathways may include portions comprising nitrocellulose, while the central pathway is formed of cellulose. One outer pathway may have a greater proportion of its length which contains nitrocellulose and/or be formed of a mixture containing a higher proportion thereof. Fine tuning of delivery characteristics of the individual fluid guiding pathways, by means of varying the material, its thickness and geometry, can be readily accomplished using printing techniques.

An example of the use of such a device is a "sandwich type" immunoassay. One outer pathway 24a/34a is composed of a single material with one dry reservoir located at 12a.The central pathway 24b/34b has a spotting point 11 located at a strategic point. The detection area 15 contains immobilized antibody. The other outer pathway 24c/34c has one dry reservoir (sited at 12c) located along its length.

A known sample volume is applied to the spotting point (which can be a hole, island or strip described herein or a hole lined with an inert wicking material (e.g., sponge) to prevent the sample from binding to the dry printed pathway) on the central pathway 24b/34b, and the buffer solution is introduced to the immersion area end of the device, e.g., by placing it in a trough of suitable buffer. The sample solution is carried up the guidance pathway to the detection area. Antigen present in the sample is "captured" by the mobilized antibodies on the detection area. The continuing flow of buffer along the central pathway will remove unbound conjugates and other substances that may interfere with the assay. During this time, buffer will be continually guided along the first outer pathway 24a/34a. As a result of this flow, the components of its dry reservoir 12a (in this example, a second antibody labelled with an appropriate enzyme) will be taken up by the buffer stream and carried towards the detection area 15. The geometry and/or nature of the chromatographic material will influence the timing of the arrival of reagents at the detection area. Labelled antibody (the conjugate) will bind with the antigen already bound on the detection area to form a complex. Continued flow will remove excess unbound, labelled antibody. Concurrent flow of buffer in the other outer pathway 24c/34c will eventually reach the dry reservoir sited at 12c, and the contents (in this example a suitable colorimetric substrate) will be taken up into the liquid flow. This pathway will usually be longest in terms of retention times. Finally, the substrate will reach the antibody-antigen-antibody complex at the detection area and produce a detectable reaction indicating presence of the analyte of interest.

FIGS. 7 and 8 show a single pathway device which includes an electrode assembly. A backing sheet 101 of insulating material (e.g., PVC film) has the form of a square with a tab 102 extending from the center of one edge. The sheet has been screen-printed in a region adjacent to the tabbed edge with an electrode assembly, in this example, having two electrodes 105 connected by conductive strips 105a to contact pads 104 on the tab 102. Subsequently, a pattern of chromatographic material (e.g., silica or cellulose) was printed, including a portion overlying (and hence, in intimate contact with) the electrodes 105. The electrodes are designed to effect an electrochemical reaction in the presence of reactant. The two-electrode arrangement consists of a working electrode and a reference electrode. In this example, the reference electrode (composed of Ag/AgCl ink) will operate as a counter electrode, acting as either a source or a sink for electrons. (A similar device could have a three-electrode arrangement, with a third electrode (counter electrode) e.g. composed of graphite. In this case, the current flow would be through the working and counter electrodes.) The composition of the working electrode material, which may be based on graphite printing ink, can be altered to suit requirements; e.g., to enhance the oxidation of a reaction product, catalytic materials can be added to the ink composition. Generally, the electrode arrangement can be built up using a series of layers e.g., conducting tracks (from the electrode face to a contact point), overlay pads (conducive to the electrode requirement) and an insulation shroud (to isolate the contacts from the solution).

The guidance pathway consists of a single track 110 with a spotting point 112 and a dry reservoir 113 deposited at a precise location. At one end of the pathway, the pattern expands to cover the entire width of the backing material. This is the immersion area 117, where the elution buffer is introduced, e.g., by placing this region of the device in a trough containing the elution buffer. The other end of the pathway broadens to cover the detection area 116 (which overlies the electrode arrangement) and thereafter, to provide a waste fluid reservoir 118.

During operation, it is envisaged that the device can be used for a "one-shot" displacement immunoassay. A typical example is the detection of the human chorionic gonadotrophin (hCG) hormone. With this assay, antigen labelled with an enzyme (e.g., glucose oxidase) is attached to immobilized antibodies at the dry reservoir site 113. Substrate for the enzymatic reaction in this example glucose is deposited, in sufficient quantity, at the detection area. The electrodes are connected by the contact pads 104 to a potentiostat poised at a selected potential. Sample solution is deposited on the spotting point 112 and buffer solution is introduced into the lower end of the device. Buffer is guided up the pathway 110 from the immersion area 117, by capillary action. The flow passes over the spotting point 112 from which it takes up the sample. When the solution reaches the dry reservoir 113 containing the labelled antigen, a displacement reaction occurs. Liberated labelled antigen is carried in the buffer stream to the detection area 116f where the enzyme undergoes a reaction with the substrate present at this site. The reaction of glucose oxidase with glucose is as follows:

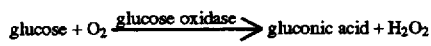

The product hydrogen peroxide can be detected amperometrically using a two- or three-electrode system. Hydrogen peroxide will be oxidized at a sufficiently high potential, and, in consequence, a current will be generated. Monitoring of this current will indicate firstly, the presence of analyte in the sample solution and secondly, the amount of analyte present. If the sample solution contains a high concentration of antigen, more displacement will occur and hence, a higher current will be generated. In contrast, a low concentration of antigen in the sample solution will produce a smaller current. Alternatively, a glucose oxidase assay system can be used in a "sandwich assay" where the conjugate, in this case glucose oxidase labelled antibody, that binds to the analyte is a non-immobilized reagent.

FIG. 9 depicts an alternative arrangement for carrying out assays using this approach. Elements corresponding to those of the first embodiment have corresponding reference numbers. A plurality of guidance pathways 121,122, 123 (three in this example) are printed onto an inert backing material 101. They coalesce at a detection area 116. Each has a spotting point 112 or a dry reservoir 113. The fluid guiding pathways differ in lengths, so that components from the reservoirs 113 and the spotting point 112 reach the detection area 116 at different times. Again, either a two- or three-electrode system can be incorporated into the design, depending on the requirements for the assay. FIG. 10 shows an equivalent device, in which the fluid guiding pathways 131, 132, 133 do not differ greatly in length but are composed, at least in part, of different materials, selected and disposed to give sequential delivery at the detection area. For example, nitrocellulose may be incorporated to give slower transit times for fluid guiding pathways or parts thereof; fibrous cellulose may be incorporated to produce faster times.

The device of FIG. 9 or FIG. 10 can be used for a "sandwich type" immunoassay where the series of guidance pathways can be used to facilitate reagent delivery and washing steps.

For example, in the FIG. 9 embodiment, the central and shortest pathway 121 has a spotting point 112, for sample deposition. Antibodies, specific to hCG, are immobilized on the surface of the detection area 116. Guidance pathway 122 is longer and contains a dry reservoir 113 where antibody labelled with enzyme (glucose oxidase) is deposited. The third and longest guidance pathway 123 has a dry reservoir 113 containing glucose (the substrate for the enzyme reaction). Again, the electrodes are connected to a potentiostat poised at a selected potential during the detection period.

Following application of the sample solution to the spotting point, the lower end of the device is immersed into a trough of buffer. The buffer travels up the fluid guiding pathways by capillary action. On the central pathway 121/131, the sample is carried along by the moving buffer onto the detection area 116. Here, antigen present in the sample is captured by antibodies immobilized at this area. The continuing flow of buffer will remove any sample components that are not bound. During this period buffer will also track along the second longest pathway 122 (or the second slowest pathway 132), taking up the second (enzyme labelled) antibody from the reservoir 113. This flow will reach the detection area after the sample, and the labelled antibody will form a sandwich complex with the antigen-antibody formation already immobilized at the detection area. Continued buffer flow from both guidance pathways will remove unbound labelled antibody from the detection area. Finally, the buffer flow in the longest, and often the slowest, pathway 123/133 will deliver the enzyme substrate (glucose) to the detection area, and the enzyme reaction will take place. Again, the current generated by the amperometric oxidation of the product, hydrogen peroxide, can be determined. The magnitude of this current will be determined by the concentration of analyte in the sample and hence, the antibody-antigen-antibody complex formed at the detection area.

In addition to performing immunoassays, the proposed device can be used for carrying out hybridization assays, based on the specific binding of nucleic acid sequences with complementary sequences. The design of the device allows different buffers to be used to alter the stringency of the hybridization. Traditional hybridization-based detection systems are time-consuming and involve several steps, thus requiring a trained operator. The use of this device will be simpler and more rapid. This will allow the development of a range of assays with medical, food and environmental applications.

A number of different nucleic acid assay formats can be envisaged. A label, such as the enzyme glucose oxidase, may be incorporated such that electrochemical detection of the reaction product can be carried out as described for the immunoassay. In some assay formats, it will be the sample nucleic acid which is labelled by the user. For example, a target single-stranded nucleic acid sequence is immobilized on the detection area. When the end of the device is immersed in the sample solution, the sample, labelled with the enzyme, travels up the chromatographic fluid guiding pathways, and, as it flows over the detection area, the complementary analyte sequence is captured. Using a two-track system (a simplified version of FIGS. 9 or 10), the enzyme substrate is delivered, after a suitable time delay, for detection of the label now present on the detection area. Alternatively, the labelled sample could be applied to a spotting point, and a buffer would then transport the sample to the target and wash away any unbound sample before the enzyme substrate is delivered. In the another arrangement, the sample is placed directly onto the target area over the electrodes. In this case, it may be necessary to incorporate an impermeable barrier around the sides of a sample well in order to prevent sample witking away from the area before all of the analyte sequence has been captured. The use of a sample well also allows the possibility of incorporating a membrane over the well. This could carry out some sample pretreatment, e.g., removing debris from analyzed cell preparation.

In order to make the labelling step simpler for the user, a specific binding pair system such as the biotin/streptavidin system could be used. In this assay, the user would carry out biotin labelling of the sample. This is a standard and straightforward procedure, e.g., using the PCR technique. The sample would then be applied to a spotting point on a fast or short track or directly to the detection area which has an immobilized target sequence complementary to the analyte sequence. The device will be dipped into a buffer which will travel rapidly up the first track, so as to deliver any sample applied to the spotting point to the target area and wash away any unbound sample. A second, slower track will deliver a streptavidin-enzyme conjugate to the target area. The streptavidin binds to the biotin label and is thus trapped on the electrode with any sample of complementary sequence to the target. Excess conjugate continues to travel into the waste reservoir before the longest track delivers the enzyme substrate for electrochemical detection.

Further assay formats are possible in which the user does not carry out any labelling. The first of these is a displacement type assay. In a dry reservoir on the shorter track, there will be a double-stranded nucleic acid sequence. One of the strands will be immobilized, whereas the complementary strand will be mobile and labelled with an enzyme. In general, this labelled strand will be only partially complementary, e.g., being shorter than, and/or containing a mismatch. The sample sequence (arialyre) will be more complementary. Thus, as the sample travels up the device, its complementary sequences will displace the labelled strand. This will then continue to move up the track and will be recaptured by a target sequence immobilized on the detection area, thus trapping enzyme label on the electrode before the longer track delivers the substrate.

A further refinement is the use of a "sandwich" type hybridization. In this two-target nucleic acid, sequences are used. These are complementary to opposite ends of the sample sequence, thus, when all three sequences are present, the sample forms a link between the two targets. Target 1 could be labelled with an enzyme and placed in a dry reservoir on the shorter track. Target 2 will be immobilized on the detection area. As the sample travels up the device, it first hybridizes to Target 1 and therefore is labelled and then captured by Target 2 as it flows over the detection area. Alternatively, a hybridization between sample and Target 1 could be carried out in a tube prior to applying the mixture to a spotting point. As with the other assays, the enzyme substrate is delivered after a suitable interval to allow for removal of unbound sample by the buffer flow. This approach, which incorporates two hybridization steps, will allow the development of highly specific assays.

A further development of this type of assay is the incorporation of naturally occurring or recombinant protein peptide receptors, e.g., from cell surfaces, as the affinity agent. In addition to receptors purified from cells, synthetic peptides mimicking the binding site of whole cell receptors or protein binding proteins could be used. These may be more stable and easier to manipulate than whole receptors. The receptor will be immobilized on the detection area. Alternatively, peptides that bind receptors or other analytes could be immobilized. A competitive or a displacement assay format could be used. In the first of these analyte conjugated to an enzyme label is present in dry reservoir and this competes for the receptor sites with the unlabelled analyte present in the sample as they low over the detection area. Thus the more analyte is that present in the sample the less label will be present on the electrode area when the enzyme substrate is later delivered by the longer track. In a displacement type assay, receptor or synthetic peptide bound to labelled analyte will be immobilized on the electrode area. Sample analyte will displace the labelled analyte as the sample flows over the electrode area. The amount displaced will be proportional to the amount of analyte in the sample. The remaining label is then detected electrochemically when the longer track delivers the substrate.

In a third possibility a receptor is used as the mobile labelled element. The ligand for the receptor is immobilized over the detection area and labelled receptor is placed in a dry reservoir on the shortest/fastest track. Sample is applied to this track and as it is carried up the device it interacts with the labelled receptor. As this then flows over the detection area, receptor which has not bound ligand present in the sample becomes bound to the immobilized ligand. Thus the label trapped on the detection area is inversely proportioned to the ligand concentration in the sample. Receptor bound to sample ligand continues to flow into the waste reservoir. A slower/longer track delivers the label substrate for detection of the receptor trapped in the detection area.

In a further variant a mobile receptor or binding protein is captured by antibody immobilized over the detection area. The ligand for the receptor is immobilized on the same pathway but upstream of the reservoir containing labelled receptor. Sample is applied to this track and as it is carried up the device it interacts with the labelled receptor. Receptor which has not interacted with ligand in the sample is trapped by the immobilized ligand sited further along the pathway.

Any receptor which has bound ligand from the sample passes over the immobilized ligand and is captured at the detection area. Thus the label trapped on the detection area is proportional to the ligand concentration in the sample.

It is envisaged that other enzyme systems can be used to produce a signal that could be detected electrochemically. A further refinement of the assay would be to incorporate a trapping layer to cover the electrode area, with the aim of concentrating the electrochemically active product from the enzyme reaction (e.g., $H_2O_2$ or mediator, such as ferrocene or hexacyanoferrate) by specifically retarding its removal from the detection area, leading to an enhanced signal at the electrode. This approach could significantly improve the detection of low concentrations of analyte in a given sample solution.

Any of the designs outlined in FIGS. 1, 5, 6, 8, 9 and 10 could form the basis of a multi-analyte and/or multi-sample analysis, whereby the designs can be multiplied to form an integral analysis system. The analysis system can be printed as an array of dedicated fluid guiding pathways and detectors on a single strip of suitable backing material. The construction would permit for each analyte individual optimized designs of chromatographic materials, thicknesses and geometries of fluid guiding pathways, dry reservoir sites and positioning of electrodes. Furthermore any combination of designs can be used to form an optimized integral analysis system. For example, the designs outlined in FIGS. 8 and 10 may be printed on a single strip of backing material.

EXAMPLE 1
Screen Printed Guidance Pathways for Optical Detection

Assay devices were prepared for the detection of human chorionic gonadotrophin (hCG), as shown in FIG. 5. Each has a backing sheet on which a pattern of chromatographic material has been deposited to define an immersion area 13, a reservoir 16, and three fluid guiding pathways 24$a,b,c$ of different lengths extending from the immersion area 13 to the reservoir 16. The fluid guiding pathways coalesce at a junction region or merged zone 15 adjacent the reservoir to which they are connected by a single pathway.

Provision of Pathway Pattern

The chromatographic material or matrix was silica, of a grade used as a separation matrix for HPLC (5μ Spherisorb, available from Phase Separations, Clwyd, GB). It was mixed with dry powder of a binder (calcium phosphate or calcium sulphate) (5 % by weight). The mixture was slurried with 2-butoxyethyl acetate.

A backing sheet (P.V.C.) was cut to shape and coated on one side with matt emulsion paint prior to printing the silica. It was dried at 40° for 1 hour.

A conventional screen printing apparatus was provided with a screen on which the desired pattern was defined in a conventional manner. For the first printing step, this was the entire pattern shown in FIG. 5 except for the junction region 15. The prepared backing sheet as located under the screen. The slurry was applied to the screen by means of a rubber squeegee. Slurry passed through the screen to provide the pattern on the painted surface of the backing sheet. The sheet was removed and allowed to dry at 40° for 1 hour. In a second printing step using the same procedure, the junction region was printed using functionalized Spherisorb (also available from Phase Separations).

Preparation of Analytical Device

Various reagents were applied to patterned sheets from step (a). In the example this was done manually, but for mass production it could be carried out by further printing steps, e.g., screen printing, ink jet printing or air brush printing.

A solution of antibodies specific to hCG was deposited over the junction region, to form a detection region 15. This was followed by incubation at 4°C. for 12$h$. The detection area was washed several times with distilled water and allowed to dry in air at a temperature not greater than 45°. (Either room temperature or 37° was generally used.) Bovine serum albumin was added to block any active sites which had not reacted with the antibodies specific to hCG, and the sheet was incubated at 4°C. for 1 hour. The detection area was washed several times with distilled water and allowed to dry.

Labelled antibodies to hCG were deposited at a reservoir site 12$c$ on the pathway 24$c$ of intermediate length. Labelling involved conjugation to glucose oxidase. The labelled antibodies were applied in a buffer solution which was allowed to dry under the same conditions as the bound antibodies. The bound antibodies and the mobile antibodies in the reservoir both bind to hCG but they recognize different epitopes in this example.

A dry deposit of a colour-producing substrate (o-dianisidine and peroxidase) for the enzyme was formed at reservoir site 12$a$ on the longest pathway 24$a$.

A spotting point 11 was indicated on the shortest pathway 24$b$ by marking with a conventional non-aqueous ink on the surface of the pathway or on the adjacent portion of the backing sheet.

Use

Two devices were tested. A test sample of buffer containing hCG was applied to the spotting point 11 of one, "test", device, while a corresponding volume of buffer was applied to the spotting point 11 of the other, "control", device. The devices were placed in a tank of buffer so that their immersion areas 13 were substantially immersed. The passage of solvent fronts up the fluid guiding pathways could be observed. In less than 10 minutes, all fluid guiding pathways had been traversed. The detection region 15 of the control device had developed strong colour, due to peroxidase-catalyzed oxidation, by hydrogen peroxide, of O-dianisidine to a brown product. The detection region 15 of the test device was almost uncoloured.

EXAMPLE 2
Screen Printed Guidance Pathways for Electrical Detection of Analytes Devices as shown in FIG. 9 were prepared. PVC sheet was cut to shape and painted (as in Example 1) to provide the backing sheets 101. Several screen-printing steps were then performed in register: (a) with Ag/AgCl ink to form the reference electrode; b) with graphite ink to form the working electrode, the conductive strips 105$a$ and the contact pads 104; (c) with a resin ink to insulate the conductive strips; and (d) with a silica slurry as in Example 1, to form the pathway pattern, including the detection area 116 applied over the electrodes 105. Antibodies specific to hCG were immobilized in the detection area. Bovine serum albumin was then ink-jet printed over the detection area to infill between bound antibody molecules and thus prevent non-specific binding. GOD-labelled antibody is deposited as a dry reservoir on pathway 122. Glucose is deposited as a dry reservoir on the longest pathway 123. A spotting point 112 is marked on the shortest track 121.

For use, a potentiostat was coupled to the contact pads 104 of one device. A sample containing hCG was applied to the spotting point. The immersion area 117 was immersed in buffer. The current passed by the potentiostat was monitored. The initial low baseline level rose rapidly once the buffer had conveyed the sample, the labelled GOD and the glucose to the detection area. Current was plotted against time. Successive experiments using identical devices with different amounts of HCG in the applied sample showed that the height of the peak in the plot correlated with the amount of hCG in the sample.

EXAMPLE 3
Screen Printed Guidance Pathways for Electric Detection of HCG

Screened printed test cards were prepared with guidance pathways for the detection of hCG analyte as shown in FIG. 11. Test cards were manufactured using PVC backing sheets (400µ) approximately 45 mm×30 mm in size, which are suitable for insertion into a portable, hand-held reader.

Test cards were screen printed using a screen printer from DEK Printing Machines Ltd. (model 247). Each region of a test card was printed using a defined pattern dictated by the screen used for printing, as shown in FIG. 11. Screens were selected based on the particulate and solvent composition of the inks used for printing. For printing of Ag conduction tracks to electrodes 200, Ag/AgCl electrodes 210, carbon conductivity strips 220, working electrode base pad 230, insulation shroud 240, working electrode 250, cellulose acetate membrane 260, stainless steel screens of 200 counts per inch mesh size were used with an emulsion thickness of 23µ and an angle of orientation of 45°. For printing of silica gel fluid guiding pathways 270 and 275, large phenyl silica fluid guiding pathways 280, and small phenyl silica fluid guiding pathways 290, stainless steel screen of 125 counts per inch mesh size were used with an emulsion thickness of 23µ and an angle of orientation of 45°.

Test cards with printed regions were made as follows:

(a) PVC backing sheets (400 µmm thickness) were sized (45 mm×30 mm) using a guillotine to form test cards.

(b) Matt vinyl emulsion paint (crown vinyl matt, Crown Decorative Products Ltd., United Kingdom) painted three times over the entire area of a test card and dried for 30 minutes at 40°C. between each coat.

(c) Two Ag conduction tracks 200 (1 layer) (silver ink electrodag 477SS RFU, Acheson Colloids, Prairie Rock, Plymouth, United Kingdom) were printed for the working and reference/counter electrodes. Following deposition the test cards were left to dry for 30 minutes at 40°C.

(d) An Ag/AgCl reference electrode 210 (1 layer) (10% Ag, Materials Characterization & Analysis Services, Melbourne Science Park, Moat Lane, Cambs, United Kingdom) was printed onto the vinyl painted PVC test card in an orientation parallel to the guidance path flow. Following deposition the cards were left to dry for 30 minutes at 40°C.

(e) A carbon base pad 230 (graphite ink electrorag 423SS, Acheson Colloids) of the working electrode and two conductivity strips (graphite ink electrorag 423SS) running the full length of the card were simultaneously printed using the same screen.

(f) An insulation shroud 240 (1 layer) was printed using a organic solvent (matt vinyl white, Apollo Colours Ltd, Plumstead, London, United Kingdom) and allowed to dry for one hour at 40°C. Using the same screen as for the insulation shroud, a matt vinyl emulsion paint (2 layers) (same paint as Step b) was printed over the insulation layer and allowed to dry for 30 minutes at 40°C.

(g) A working electrode 250 (2 layers) was printed using a working electrode ink prepared as 5mg of MCA4 (a catalytic carbon powder based on rhodinized carbon, supplied by Materials, Characterization & Analysis Services) in 5ml of a 3% (w/v in distilled water) hydroxyethylcellulose solution. The working electrode was printed perpendicular to the fluid flow in the fluid guiding pathway. The solution was stirred for 1 hour on a rotary stirrer to achieve a homogeneous solution. After each application the ink was allowed to dry for 30 minutes at 40°C.

(h) The electrical continuity of both the working and reference/counter electrodes was tested after the printing of working electrode to ensure good contact between the electrode faces and their respective conduction tracks.

(i) A main channel 270 (four layers) and glucose feeder pathway 275 (four layers) were printed using a silica gel paste solution prepared as 7 g of high purity grade silica gel without binder (average particle size 5–25µ and average pore diameter 60 Å), 3 g calcium phosphate (dibasic) binder and 14 g of a 3% (w/v in water) hydroxyethylcellulose solution (ambient temperature, at 20°C.). The solution was stirred by hand using a metal spatula until a uniform consistency was achieved. After each printing the four layers, cards were dried for 45 minutes at 40° C.

(j) A cellulose acetate membrane 260 (2 layers) was printed using a cellulose acetate solution prepared as 4% (w/v) cellulose acetate powder (acetyl content was approximately 40%) in a 1:1 (v/v) solution of acetone and cyclohexanone. After each printing the cards were dried for 30 minutes at room temperature.

(k) The phenyl silica (Phase Separations Ltd, Deeside Industrial Park, Clwyd, UK) region surrounding the electrode 280 (4 layers) was printed using a phenyl silica solution prepared as phenyl silica paste mixed with a 10% hydroxyethylcellulose solution in water in a 2:1 (w/v) ratio. Hydroxyethylcellulose acts as an organic binder to allow the paste to be printed. The phenyl silica solution was stirred by hand using a glass rod to achieve a uniform consistency. After each printing the cards were dried for 45 minutes at room temperature. The phenyl silica paste was prepared as follows:

(1) Phenyl silica particles (2g) of 5µ were weighed in a glass bottle, washed twice with PBS (phosphate buffered saline) buffer and spun down using a centrifuge (5 minutes, at 4000G).

(2) The phenyl silica particles were then incubated in a 5% BSA in PBS buffer solution at 4°C. on rotary stirrer for 12 to 24 hours.

(3) The resulting BSA blocked phenyl silica was washed three times with PBS buffer to remove unattached BSA, then resuspended in a solution of goat serum and PBS buffer (1:1 ratio). Goat serum was included in order to block all of the non-specific binding sites not occupied by the BSA protein.

(4) The phenyl silica paste in goat serum was incubated at 4°C. for 15 hours then washed three times in PBS buffer and stored at 4°C. until required.

(l) A phenyl silica/capture antibody region 290 (2 layers) was printed using a phenyl silica capture antibody solution prepared as follows:

(1) Phenyl silica particles (2g) (5 micron) were weighed in a small glass bottle, washed twice with PBS buffer and spun down using a centrifuge (5 minutes, at 4000G).

(2) The silica particles were then suspended in 5ml of PBS buffer and antibody solution (1.0ml, 10.1 mg per ml, goat polyclonal anti-βhCG) was added to the silica. Following a complete mixing, the solution was incubated for 12 to 24 hours at 4°C. on a rotary stirrer.

(3) The phenyl silica/antibody mixture was spun down using a centrifuge (5 minutes, 4000G) and washed three times in PBS buffer to remove unattached antibodies.

(4) Following washing the mixture was incubated with a 5% BSA in PBS buffer solution for 12 to 24 hours at 4°C., on a rotary stirrer.

(5) The BSA blocked phenyl silica was washed three times with PBS buffer to remove unattached BSA, then resuspended in a PBS buffer/goat serum (1:1 ratio) solution for 16 hours at 4° C.

(6) After this final blocking stage, the BSA/goat serum blocked silica was washed three times with PBS buffer and stored at 4° C. until required. After each printing the cards were allowed to dry for 45 minutes at room temperature.

(m) Glucose solution (2 µl of 0.1M solution) was applied halfway 300 along the glucose delivery pathway and dried for 45 minutes at room temperature. The 0.1M glucose solution was prepared in 0.1M sodium phosphate pH 6.8 containing 0.1M potassium chloride and stored at 4° C. for 18 hours to allow for mutarotation.

(n) Blocked antibody/conjugate 320 (1.5 µl) was applied onto the larger coversheet (30 mm×10 mm) and dried for 1 hour at room temperature. Blocked antibody/conjugate (goat polyclonal anti-α-hCG/glucose oxidase mixed 1:1 with 2% BSA in water) solution was prepared by mixing antibody conjugate with BSA to give a final blocking protein concentration of 1%. Following drying, a narrow strip of masking tape fixed the larger coversheet over the main (phenyl silica) pathway such that the dried conjugate was approximately 5–7 mm upstream of the working electrode area. The second, smaller, coversheet (2×15 mm) is an option and can be positioned over the secondary glucose delivery pathway. Its function is, if required, to accelerate the flow of fluid through this pathway.

(o) The completed test card was stored at 4° C. until use.

FIG. 12 shows a three dimensional cross-section of the detection zone in FIG. 11 showing the PVC backing sheet 310, emulsion paint 320, carbon base pad 330, catalytic carbon 340, cellulose acetate membrane 350, phenyl silica-antibody layer 360, PVC cover-sheet 370, and conjuage 320.

Steps a through n are the preferred order for making such test cards. The order of the steps may be adapted to meet specific needs of other assay reagents. Only some steps may be completed to produce some of the most simplied embodiments of the invention, i.e., printing of a fluid guiding pathway with a detection zone.

Test cards were tested using a buffer solution comprising of 0.1M sodium phosphate and 0.1M potassium chloride pH 7.0 with or without antigen (1,000mIU of hCG (final concentration)). In order to demonstrate applicability of the test to operation in complex media, tests were also performed in diluted urine from a nonpregnant female with and without antigen. The urine was diluted 1:1 with a buffer solution composed of 0.1M sodium phosphate containing 0.1 potassium chloride pH 6.8. This sample solution was used as the negative control. To prepare a positive control, the urine/buffer solution was spiked with hCG to give a final concentration of 500mIU. Tests were performed at an applied potential of +350mV (versus an Ag/AgCl electrode). Presence of an analyte was indicated by an increase in current due to oxidation of $H_2O_2$ generated by the captured immuno-enzyme-analyte complex.

FIG. 13 shows the electrochemical response of a negative control test card. No antigen (false positive) was detected, as the current maintained a steady-state for over 140 seconds. No antigen was detected in the negative control urine samples as well.

FIG. 14 shows the electrochemical response of a positive control test card. Antigen (true positive) was detected within 120 seconds, as the current linearly increased for over 140 seconds. Antigen was detected in the positive control urine samples as well.

EXAMPLE 4
Cellulose Acetate Size Exclusion Membrane for the Detection Zone

Cellulose acetate membranes were tested for their ability to reduce the loss of a detectable signal by reducing non-specific binding in the detection zone. Test cards were prepared as described in Example 3, except for changes to the method of test card preparation stated herein. Membranes were printed on top of test card working electrodes as mixtures of cyclohexanone and acetone with a range of cellulose acetate concentrations (from 0.5% to 6% w/v) and were tested using the glucose oxidase assay system discussed herein. Concentrations of cellulose acetate from 3% to 5% (w/v in cyclohexanone and acetone 1:1) reduced background noise and improved reproducibility, and accuracy of test card assays. Cellulose acetate concentrations less than 3% (w/v) (0.5% to approximately 3%) were not suitable for printing inks, as the viscosity did not permit printing. Phenyl silica could be printed directly over the cellulose acetate membrane without disrupting the structure of the membrane. Cellulose acetate membranes prepared from a solution of cellulose acetate (4% in a 1:1 mixture of acetone and cyclohexanone) produced the best background signals, response times and printing characteristics, as well as improving the reproducibility, and accuracy of test card assays.

EXAMPLE 5
Flow Accelerators to Reduce Conjugate Retention

The use of flow accelerators to reduce undesired conjugate retention was tested using conjugate releasing reservoirs applied to PVC cover-sheets. Two types of flow accelerators were tested to decrease undesired conjugate retention in the guidance pathways and detection zone: 1) conjugates released from synthetic sponges, such as dishwashing sponges bonded to PVC coverslips and 2) conjugates released from deposits on the PVC cover-sheets.

Synthetic sponges were bonded to PVC cover-sheets using glue. Several types of sponge materials were tested for their ability to completely release dried conjugate upon hydration. The sponges were cut using a scalpel to a uniform size (15 mm long, 10 mm wide and 3 mm thick) and bonded to a PVC coversheet (30 mm long, 10 mm wide and 400 µm thick) using a commercial glue, such as bostik. Antibody conjugate (1.5 µl) 0.6 mg per ml was centrally deposited on the sponge surface at a central location upon completion of the bonding of the sponge to the PVC. The cover-sheet was positioned 5–7 mm upstream of the electrode detection zone and in capillary contact with the main pathway, in this case immediately over the main phenyl silica pathway. Masking tape affixed the cover-sheet in place.

Alternatively, conjugate was dried directly on PVC cover-sheets. Conjugate was centrally deposited as 1.5 µl on the PVC cover-sheets and left to dry for 1 hour at room temperature. Following drying, the cover-sheet was positioned 5–7 mm upstream of the electrode detection zone and in capillary contact with the main pathway, in this case immediately over the main phenyl silica pathway.

Test cards, with either conjugate releasing sponge cover-sheets or conjugate releasing PVC cover-sheets, were tested by immersing the test cards in a buffer solution and assaying for hCG using the sandwich glucose oxidase system described herein. Negative control solutions contained no antigen; positive control solutions contained a standard (500 mIU) hCG concentration. Following complete washing (until complete saturation of the silica gel on the test card), the cover-sheet was removed and 2 μl of a 0.1M glucose solution directly pipetted onto the surface of the electrode area in either conjugate releasing sponge cover-sheet or conjugate releasing PVC cover-sheet test cards. Negative controls for both types of cards clearly showed no electrochemical response from the immuno-complex indicating that unbound conjugate has been removed from the electrode site. In contrast, positive controls for both types of cards clearly showed an electrochemical response from a sample solution containing hCG.

We claim:

1. A method of manufacturing a fluid transport device, which method comprises providing a backing sheet and printing onto said backing sheet a material comprising silica, cellulose, a silica derivative or a cellulose derivative to provide a pattern having a liquid application zone with at least two fluid guiding pathways extending from the liquid application zone and leading to a merged zone, said material being printed in a manner that provides for liquids or solutes to flow from said liquid application zone to said merged zone at different transit times.

2. The method of claim 1 wherein each guiding pathway is printed with a material that differs in chemical or physical composition to produce a different flow rate for each guiding pathway so that transit times differ for liquids or solutes through said at least two different fluid guiding pathways.

3. The method of claim 2 where at least one guiding pathway comprises sufficient nitrocellulose to retard flow of a solute along it.

4. The method of claim 2 wherein at least one guiding pathway comprises sufficient fibrous cellulose to facilitate rapid flow along it.

5. The method of claim 2 wherein at least two guiding differ in length.

6. The method of claim 2 wherein at least one pathway portion is produced by applying a mixture of material for providing a fluid pathway and a reagent substance.

7. The method of claim 6 wherein either before or after said application of material for providing at least two fluid pathways, an electrode assembly is applied to the backing sheet by a printing technique; at least one fluid pathway having a detection zone which overlies or underlies at least part of the electrode assembly.

8. The method of claim 7 wherein the electrode assembly is applied by screen printing.

* * * * *